United States Patent
Dutriez et al.

(10) Patent No.: US 11,002,716 B2
(45) Date of Patent: May 11, 2021

(54) METHOD OF RESOLVING DEFINED KNOWN OR SUSPECTED ALLERGENS IN A COMPLEX MIXTURE OF PERFUME INGREDIENTS, AND COMPOSITIONS

(71) Applicant: GIVAUDAN SA, Vernier (CH)

(72) Inventors: Thomas Dutriez, Sergy (FR); Neil Owen, Romney Marsh (GB)

(73) Assignee: GIVAUDAN SA, Vernier (CH)

( * ) Notice: Subject to any disclaimer, the term of this patent is extended or adjusted under 35 U.S.C. 154(b) by 173 days.

(21) Appl. No.: 16/098,741

(22) PCT Filed: May 29, 2017

(86) PCT No.: PCT/EP2017/062853
§ 371 (c)(1),
(2) Date: Nov. 2, 2018

(87) PCT Pub. No.: WO2017/207467
PCT Pub. Date: Dec. 7, 2017

(65) Prior Publication Data
US 2019/0145942 A1 May 16, 2019

(30) Foreign Application Priority Data
May 30, 2016 (GB) .................................. 1609467

(51) Int. Cl.
*G01N 30/46* (2006.01)
*C11B 9/00* (2006.01)
*G01N 30/86* (2006.01)
*G16C 20/20* (2019.01)
*G16C 20/70* (2019.01)
*B01J 20/26* (2006.01)
*B01J 20/281* (2006.01)

(52) U.S. Cl.
CPC .............. *G01N 30/463* (2013.01); *C11B 9/00* (2013.01); *G01N 30/8644* (2013.01); *G01N 30/8686* (2013.01); *G01N 30/8693* (2013.01); *G16C 20/20* (2019.02); *B01J 20/264* (2013.01); *G01N 30/482* (2013.01); *G16C 20/70* (2019.02)

(58) Field of Classification Search
CPC .............. G01N 30/463; G01N 30/482; G01N 30/8644; G01N 30/8686; G01N 30/8693; G16C 20/20; G16C 20/70
See application file for complete search history.

(56) References Cited

U.S. PATENT DOCUMENTS

2007/0039375 A1* 2/2007 Chaintreau .......... G01N 30/463
73/23.41
2015/0299614 A1 10/2015 Flachsmann et al.
(Continued)

OTHER PUBLICATIONS

John V. Seeley, Carly T. Bates, James D. McCurry, and Stacy K. Seeley. "Stationary phase selection and comprehensive two-dimensional gas chromatographic analysis of trace biodiesel in petroleum-based fuel". Journal of Chromatography A, vol. 1226, pp. 103-109. (Year: 2012).*
(Continued)

*Primary Examiner* — Natalie Huls
(74) *Attorney, Agent, or Firm* — Norris McLaughlin PA

(57) ABSTRACT

Analytical methods that can be employed to reliably separate known or suspected allergens in a complex mixture of fragrance ingredients are described.

11 Claims, 2 Drawing Sheets

(56) References Cited

U.S. PATENT DOCUMENTS

Figure 1:
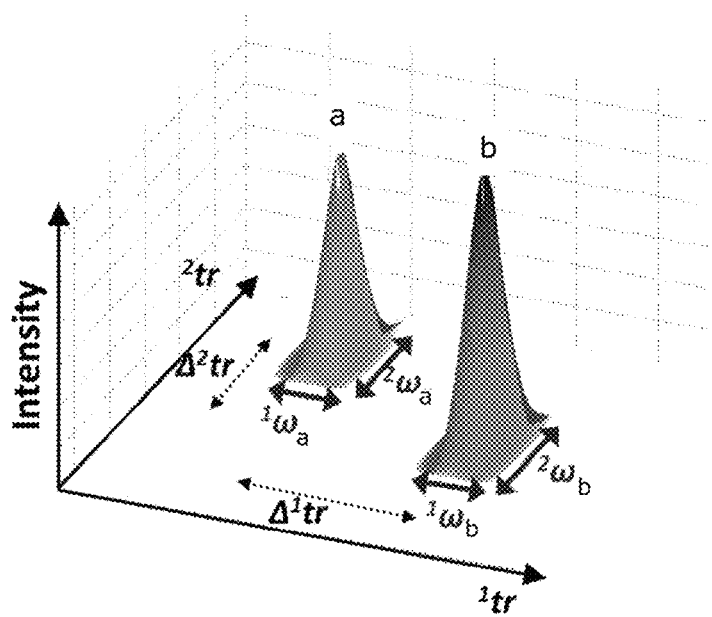

| | | | |
|---|---|---|---|
| 2017/0241960 A1* | 8/2017 | Contreras | B01D 53/025 |
| 2018/0148666 A1* | 5/2018 | Antoniotti | C11B 9/0042 |
| 2020/0138071 A1* | 5/2020 | Shi | A23L 27/215 |

OTHER PUBLICATIONS

International Search Report and Written Opinion of the International Searching Authority for corresponding application PCT/EP2017/062853 dated Sep. 12, 2017.

C. Cordero, et al; "Identification, quantitation and method validation for the analysis of suspected allergens in fragrances by comprehensive two-dimensional gas chromatography coupled with quadrupole mass spectrometry and with flame ionization detection"; Journal of Chromatography A, 1150 (2007), p. 37-49; (Elsevier—SchienceDirect).

R. Shellie, et al; "Quantitation of suspected allergens in fragrances (Part I): evaluation of comprehensive two-dimensional gas chromatography for quality control"; Flavour and Fragrance Journal, 2004; vol. 19; p. 91-98, Wiley InterScience.

M.S. Dunn, et al; "Targeted multidimensional gas chromatorgraphy for the quantitative analysis of suspected allergens in fragrance products"; Journal of Chromatography A; 1130 (2006); p. 122-129; (Elsevier; ScienceDirect).

G. Purcaro, et al; "Evaluation of a Rapid-Scanning Quadrupole Mass Spectrometer in an Apolar x Ionic-Liquid Comprehensive Two-Dimensional Gas Chromatography System", Anal. Chem., 2010; vol. 82; p. 8583-8590.

H. Leijs, et al: "Quantitative Analysis of the 26 Allergens for Cosmetic Labeling in Fragrance Raw Materials and Perfume Oils"; Journal of Agricultural Food Chemistry, 2005, vol. 53, No. 14, p. 5487-5491.

P.Q. Tranchida, et al, "Four stage (low) flow comprehensive gas chromatography quadrupole mass spectrometry for the determination of recently highlighted cosmetic allergens", Journal of Chromatography A., vol. 1439, 2016, pp. 144-151.

C. Cordero, et al, "Potential of the reversal-injection differential flow modulator for comprehensive two-dimensional gas chromatography in the quantitative profiling and fingerprinting of essential oils of different complexity", Journal of Chromatography A, vol. 1417, pp. 79-95, 2015.

C. Cordero, et al, "Evaluation of different internal-diameter column combinations in comprehensive two-dimensional gas chromatography in flavour and fragrance analysis", Journal of Separation Science, vol. 31, No. 19, pp. 3437-3450, 2008.

L. Mahe, et al. "Global Approach for the selection of high temperature comprehensive two-dimensional gas chromatography", Journal of Chromatography A, vol. 1218, No. 3, pp. 534-544, 2011.

GB Search report for corresponding application GB 1609467.4 dated Mar. 31, 2017.

* cited by examiner

METHOD OF RESOLVING DEFINED KNOWN OR SUSPECTED ALLERGENS IN A COMPLEX MIXTURE OF PERFUME INGREDIENTS, AND COMPOSITIONS

This is an application filed under 35 USC 371 based on PCT/EP2017/062853 filed 29 May 2017, which in turn was filed based on GB 1609467.4 filed 30 May 2016. The present application claims the full priority benefit of these prior applications and herein incorporates by reference the full disclosures of these prior applications.

FIELD OF THE INVENTION

This disclosure is related to a method of detecting analytical targets, such as known or suspected allergenic compounds, in complex mixtures of ingredients, and in particular complex mixtures of fragrance ingredients. It is also related to a method of preparing complex mixtures, and particularly fragrance compositions, that are free or substantially free of said analytical targets, particularly known or suspected allergenic compounds, and to complex mixtures prepared by said method.

BACKGROUND OF THE INVENTION

Fragrance compositions used in both fine perfumery and functional perfumery very often consist of complex mixtures that may contain tens or even hundreds of fragrance ingredients.

Furthermore, some fragrance ingredients that are considered to be single ingredients from the perspective of a perfumer (such as essential oils) may actually contain many hundreds of components and impurities, some of which may be considered to be potentially allergenic substances within the terms of the $7^{th}$ Amendment of the Cosmetics Directive, Directive 2003/15/EC.

Indeed, currently, there are 24 ingredients that are categorized as potential allergenic substances under the Directive, and the possibility cannot be discounted that more substances will be similarly categorized in the future. For companies desirous of adding fragrance compositions to personal care or cosmetic products, it will be important to know if those fragrance compositions contain significant levels of any impurities that may be considered to be potential allergenic compounds under the Directive.

Chromatographic techniques are already well known in the art for separating complex mixtures. Most high resolution gas chromatography techniques have been developed to separate aliphatic and aromatic hydrocarbons. However, chemical compounds that have pleasant odours and which are therefore interesting as perfume ingredients tend to possess substantially similar chemical and physical properties, such as molecular weight, polarity and the like. And because of these similar properties, potentially allergenic ingredients contained in complex fragrance compositions, may be difficult to resolve and quantify analytically.

New and higher resolution analytical approaches, characterized by stringent prerequisites in terms of analytical resolution and selectivity are required.

Comprehensive two-dimensional chromatography, also referred to as GC×GC or 2D-GC in the literature, is a known method for separating complex mixtures of analytes. In GC×GC, a complex mixture is separated on a first capillary column comprising a first stationary phase $^1D$ before being separated a second time, portion wise, on a second capillary column comprising a second stationary phase $^2D$, see for example Marriott et al., "Multidimensional Gas Chromatography" in "Encyclopedia of Separation Science, Ian D. Wilson (Editor), Elsevier, 2000, ISBN: 978-0-12-226770-3, pages 536-544.

The main advantage of comprehensive two-dimensional chromatography over conventional high resolution chromatography is its much higher peak capacity, which may be 9 to 11 times larger than that of the latter. The term "peak capacity" describes the number of peaks that can be fitted on to a chromatogram between two defined points, each peak being separated from its neighbour by a defined amount. Theoretically, maximum peak capacity is achieved when two stationary phases are orthogonal, that is, the mechanisms of separation in two dimensions are independent of each other. For this reason, it is customary to use combinations of polar×apolar or apolar×polar columns.

Peak capacity is commonly used to assess the quality of a stationary phase or of a combination of stationary phases, and optimization of the performance of chromatographic separation process commonly involves maximizing the peak capacity (see for example L. M. Blumberg et al., J. Chromatogr. A 1188 (2008) 2-16. L. M. Blumberg et al., J. Sep. Sci. 31 (2008) 3352-3357). Selection of stationary phases is typically based on an optimization of peak capacity, and the process is iterative and can be laborious.

The use of GC×GC method for determining the composition of complex mixtures, such as natural essential oils is known. In recent years, several authors have attempted to use this method to resolve and then quantify a limited number of potentially allergenic substances that may be present in such essential oils: see for example G. Purcaro et al. Anal. Chem. 2010, 82, 8583-8590; M. S. Dunn et al. J. Chrom. A, 1130 (2006) 122-129; H. Leijs et al. J. Agric. Food Chem. 2005, 53, 5487-5491; C. Cordero et al. J. Chrom. A, 1150 (2007) 37-49; R. Shellie et al. Flavour Fragr. J. 2004; 19: 91-98.

However, in all these studies, the number of suspected allergens that has been separated and then quantified was limited to 24. Although it has been possible to overcome the problem of separating the current list of 24 of suspected allergens, existing techniques are insufficient in regard to the increasing number of substances that are suspected to be potentially allergenic, and which may come under scrutiny by regulatory authorities. Indeed, a new extended list of suspected allergens and regulated substances has been drawn up, comprising 95 substances, set forth in Table 1 below.

The principal limitation with previous attempts to achieve such complex separation tasks lies in the systematic selection of a first apolar stationary phase and, in most cases, selection of a second polar phase to maximize the difference of polarity between both stationary phases. Typically, a first, apolar stationary phase comprising 95% and more poly (dimethyl-siloxane) combined with a second, polar stationary phase comprising polyethylene glycol, or a second intermediate polarity stationary phase were used. In one case, the first stationary phase was a 100% poly(dimethyl-siloxane) apolar phase and the second stationary phase had an intermediate polarity (C. Cordero et al. J. Chrom. A, 1150 (2007) 37-49). However the applicant found that these particular combinations of stationary phase were unable to resolve a mixture containing the extended list of substances.

However, applicant systematically examined and found that conventional 2D-GC set-ups combining a first apolar column with a second polar column, or a first apolar column with a second mid polar column, or a first polar column and a second apolar column, did not provide the desired 2D separation efficiency of mixtures containing the extended list of substances.

Applicant has found that relying on peak capacity to select the combined stationary phases in a comprehensive two-dimensional gas chromatography set-up was not sufficient for achieving the analytical resolution required to separate the aforementioned complex mixture set forth in Table 1. A high peak capacity will inform an analyst that a particular column selection is likely to increase the chance of a reasonable separation, but it will not predict that separation will be optimal for a given complex mixture.

Absent reliable and accurate analytical data regarding the presence of the 95 known or suspected allergens that may be found in fragrance compositions, consumers may have insufficient information to be sure of satisfying requirements of any existing or upcoming regulation. But beyond any consideration of regulatory issues, existing analytical techniques are simply inadequate for the skilled person to resolve and eventually quantify individual known or suspected allergens in complex mixtures of fragrance ingredients.

There remains a need to provide analytical methods that can be employed to reliably separate known or suspected allergens in a complex mixtures of fragrance ingredients, and thereby enable further identification and quantification of these allergens.

SUMMARY OF THE INVENTION

The applicant has now found a novel stationary phase selection criterion, based on clustering analysis of a group of defined analytical targets, which criterion is defined hereunder as the two-dimensional separation efficiency ($SE_{2D}$). Stationary phase combinations that in a 2D-GC set up will score a $SE_{2D}$ value above a threshold value, defined hereinbelow, will separate with good resolution said defined group of analytical targets.

The invention provides in a first aspect, a method of selecting combinations of stationary phases for two-dimensional comprehensive gas chromatography of a complex mixture, the selection being based on a Separation Efficiency parameter $SE_{2D}$, derived from a clustering analysis of defined analytical targets.

The invention provides in another aspect a method of resolving defined analytical targets in a complex mixture using two-dimensional gas chromatography, wherein the combination of stationary phases for two-dimensional comprehensive gas chromatography are selected on the basis of a Separation Efficiency parameter $SE_{2D}$, derived from a clustering analysis of defined analytical targets.

In another aspect of the invention there is provided a method of preparing a composition comprising the step of including in said composition at least one ingredient that is either not a defined analytical target, or is an ingredient that is substantially free of defined analytical targets, as determined by two-dimensional comprehensive gas chromatography, wherein the combination of stationary phases for two-dimensional comprehensive gas chromatography are selected on the basis of a Separation Efficiency parameter $SE_{2D}$, derived from a clustering analysis of defined analytical targets.

In yet another aspect of the invention there is provided a composition that is substantially free of defined analytical targets, as determined by two-dimensional comprehensive gas chromatography, wherein the combination of stationary phases for two-dimensional comprehensive gas chromatography are selected on the basis of a Separation Efficiency parameter $SE_{2D}$, derived from a clustering analysis of defined analytical targets.

DETAILED DESCRIPTION OF THE INVENTION

The present invention is based on a clustering analysis of defined analytical targets. The clustering analysis is described more fully hereinbelow. Although the invention is applicable to the separation of any defined analytical targets contained in a complex mixture in order that they can be identified and/or quantified as required, the invention is hereinafter illustrated with particular reference to a group of defined analytical targets consisting of a list of 95 known or suspected allergens set forth hereinbelow in Table 1.

If a 2D-GC set up contains a combination of stationary phases that delivers a Separation Efficiency ($SE_{2D}$) value above a certain threshold value defined hereinbelow, then the individual known or suspected allergens can be satisfactorily separated in a mixture containing all 95 of said allergens.

And it follows from this that said allergens could be identified, and ultimately separated and quantified from a complex mixture of fragrance ingredients, using techniques known in the art.

The methodology of the present invention is based on a novel metric for assessing the resolving power of a 2D-GC set-up based on a defined list of known or suspected allergens involving a clustering analysis of neighbouring peaks having a known mutual two-dimensional resolution value $Rs_{2D}$, which is defined hereunder.

The methodology is further characterized in that the clustering behaviour of the defined known or suspected allergens is based on the value of the mutual two-dimensional resolution, wherein two known or suspected allergens having mutual two-dimensional resolution ($Rs_{2D}$) value of 1 or higher are considered to be well separated, whereas two known or suspected allergens having mutual two-dimensional resolution ($Rs_{2D}$) value lower than 1 are not considered to be well separated, and therefore belong to the same cluster.

The mutual two dimensional resolution $Rs_{2D}$ is defined as the two-dimensional resolution between two neighbouring peaks, corresponding to two different defined analytical targets, on a 2D-GC contour plot, as shown in FIG. 1, and is expressed by the following equation, see J. C. Giddings, Multidimensional Chromatography: Techniques and Applications. In: Multidimensional Chromatography: Techniques and Applications (Cortes H. J. Ed), Marcel Dekker, New York (1990), which is hereby incorporated by reference.

$$Rs_{2D} = \sqrt{\left(\frac{2 \times \Delta^1 tr}{^1\omega_a + ^1\omega_b}\right)^2 + \left(\frac{2 \times \Delta^2 tr}{^2\omega_a + ^2\omega_b}\right)^2} \quad \text{Equation 1}$$

wherein
$\Delta^1 tr$ is the difference of retention times between two neighbouring peaks (a) and (b) on the first dimension (x-axis);
$\Delta^2 tr$ is the difference of retention times between the same two neighbouring peaks (a) and (b) on the second dimension (y-axis);
$^1\omega_a$ is the first dimension 6a peak width of the peak (a) (on x-axis);
$^1\omega_b$ is the first dimension 6a peak width of peak (b) (on x-axis);

$^2\omega_a$ is the second dimension 60 peak width of the peak (a) (on y-axis); and
$^2\omega_b$ is the second dimension 6a peak width of the peak (b) (on y-axis).

As a particularly useful approximation, the applicant has, however, found that equation above could be simplified into the following equation $$Rs_{2D} = \frac{1}{\sqrt{\left(\frac{2 \times \Delta^1 tr}{2 \times (M_r+1) \times P_M}\right)^2 + \left(\frac{2 \times \Delta^2 tr}{2.55 \times (^2FWHH_a + {}^2FWHH_b)}\right)^2}} \qquad \text{Equation 2}$$

where
$M_r$ is the average number of times each peak is sampled by the modulator, as described hereunder, rounded to the upper value.
$P_M$ is the 2D-GC modulation period;
$^2FWHH_a$ is the second dimension peak width of the peak (a) at half height; and
$^2FWHH_b$ is the second dimension peak width of the peak (b) at half height.

It follows from Equation 2 that two defined analytical targets being well separated from each other during the 2D-GC chromatographic process will have a relatively large $Rs_{2D}$ value, whereas two defined analytical targets being very close to each other will be characterized by a relatively small $Rs_{2D}$ value. Hence, defined analytical targets having neighbouring peaks (for example, peaks recorded with a retention time within +/−30s) with a mutual $Rs_{2D}$ value of 1 or above are well separated. In other words, the analytical process can be considered as maximal for this given defined analytical target.

Conversely, defined analytical targets having neighbouring peaks with mutual $Rs_{2D}$ values below 1 are not to be well separated. Considering a poorly separated defined analytical target, the separation performance of the analytical process for this target is determined by the value of its mutual $Rs_{2D}$ value and the number of neighbouring peaks with a mutual $Rs_{2D}$ value below 1. In other words, the resolution of the analytical process depends on the number of peaks that are present within a cluster of dimension $Rs_{2D}<1$. Illustrative examples of $Rs_{2D}$ values, related to target separation cases, are given in Example 3.

For the purpose of the present invention, defined analytical targets having no neighbouring peak with a mutual $Rs_{2D}$ value smaller than 1 are defined as singletons (S); a defined analytical target having one neighbouring peak having a mutual $Rs_{2D}$ value smaller than 1 is considered to belong to a single cluster (C); and a defined analytical target having several neighbouring peaks having mutual $Rs_{2D}$ values less than 1 are considered to belong to several clusters.

The clustering procedure and cluster counting, according to the present invention, are explained more fully in Table 8. In this Table, 17 defined analytical targets were found to have a $Rs_{2D}$ value smaller than 1 and 17 defined analytical targets were found to belong to 11 clusters, whereas 78 defined analytical targets were found to belong to Singletons.

Furthermore, the present invention defines a 2D separation efficiency parameter ($SE_{2D}$) for a 2D-GC set-up (Equation 3, below), as the percentage of the total number of defined analytical targets being resolved by a 2D-GC chromatographic process, considering than a defined analytical target belonging to a singleton has a contribution of 1, and a defined analytical target belonging to only one cluster has a contribution to $SE_{2D}$ of its mutual $Rs_{2D}$ value, whereas a defined analytical target belonging to several clusters has contributes to $SE_{2D}$ in an amount equivalent to the product of all of its mutual $Rs_{2D}$ values, as set forth in the equation below.

$$SE_{2D} = \frac{100}{n+m} \times \left( n + \sum_{i=1}^{m} \left( \prod_{j=1}^{o} Rs_{2D,ij} \right) \right) \qquad \text{Equation 3}$$

where
n is the number of Singletons;
m is the number of defined analytical targets belonging to clusters;
o is the number of clusters including a given defined analytical target; and
$Rs_{2D,ij}$ is the $Rs_{2D}$ value for a defined analytical target i in a given cluster j.

The applicant has found that a method conforming to the present invention, the Separation Efficiency ($SE_{2D}$) of a two-dimensional comprehensive gas chromatography set-up must be higher than 94%, and particularly higher than 95%. In other words, the percentage of unresolved defined analytical targets ($^nSE_{2D}$), as defined by equation (2), must be lower than 6%, and particularly lower than 5%.

$$^nSE_{2D} = 100 - SE_{2D} \qquad \text{Equation 4}$$

Any combination of stationary phases employed in a 2D GC set up that provides a ($SE_{2D}$) value above this threshold is a preferred combination in pursuance of the present invention.

Furthermore, in a more particular embodiment of the invention, the peak capacity ($n_{c,\ 2D}$) of a 2D-GC set-up, as defined in more details here under, is higher than 4000, more particularly higher than 4500.

The peak capacity is defined by equation 5 (see L. M. Blumberg et al., J. Chromatogr. A 1188 (2008) 2-16. L. M. Blumberg et al., J. Sep. Sci. 31 (2008) 3352-3357, which is hereby incorporated by reference)

$$^{obs}n_{c,2D} = \frac{2}{\pi} \times {}^{obs,1}n_c \times {}^{obs,2}n_c \qquad \text{Equation 5}$$

where
$^{obs}n_{c,2D}$ is the observed 2D peak capacity for a given 2D-GC set-up;
$^{obs,1}n_c$ is the observed first dimension peak capacity; and
$^{obs,2}n_c$ the observed second dimension peak capacity.
$^{obs,1}n_c$ is given by equation 6 (see Klee et al. J. Chrom. A 1383, 151-9 (2015)).

$$^{obs,1}n_c = \frac{(^1t_{last} - {}^1t_{first})}{(M_r+1) \times P_M} \qquad \text{Equation 6}$$

where
$^1t_{last}$ is the first dimension retention time of the last eluting compound;

$^1 t_{first}$ is the first dimension retention time of the first eluting compound;

$P_M$ is the modulation period; and $M_r$ is the number of the average number of time each peak is sampled by the modulator, as described hereunder, rounded to the upper value.

A similar equation is used for $^{obs,2}n_c$, with subscript index 2, instead of 1.

Finally, the applicant has used equation 7 for $^{obs,2}n_c$, based on the method proposed by Lan et al. Anal. Chem. 71 (1999) 709-714, which is hereby incorporated by reference, where a and b are fitting parameters for a given 2D-GC set-up. These parameters are listed in Table 10.

$$^{obs,2}n_c = \frac{\text{Ln}\left(\sqrt{a \times ^2 t_{last}^2 + b} + \sqrt{a} \times ^2 t_{last}\right)}{\sqrt{a}} - \frac{\text{Ln}\left(\sqrt{a \times ^2 t_{start}^2 + b} + \sqrt{a} \times ^2 t_{start}\right)}{\sqrt{a}} \quad \text{Equation 7}$$

As state herein above, the methodology according to the present invention can be employed to resolve any defined analytical targets from a complex mixture. However, in a particular embodiment of the present invention, the defined analytical targets are a group of 95 known or suspected allergens, as set forth in Table 1 below.

TABLE 1

| Extended list of potentially allergenic organic substances and other regulated substances | CAS# |
| --- | --- |
| Acetyl Cedrene (main isomer) | 32388-55-9 |
| Alpha Isomethylionone | 127-51-5 |
| Amyl Cinnamic Alcohol (E) | 101-85-9 |
| Amyl Cinnamic Aldehyde (E) | 122-40-7 |
| Amyl Salicylate (ISO-) | 87-20-7 |
| Amyl Salicylate (N-) | 2050-08-0 |
| Anethole Trans (E) | 4180-23-8 |
| Anisyl Alcohol | 105-13-5 |
| Benzaldehyde | 100-52-7 |
| Benzyl Alcohol | 100-51-6 |
| Benzyl Benzoate | 120-51-4 |
| Benzyl Cinnamate (E) | 103-41-3 |
| Benzyl Cyanide | 140-29-4 |
| Benzyl Salicylate | 118-58-1 |
| Camphor | 76-22-2 |
| Carvone | 99-49-0 |
| Caryophyllene Beta | 87-44-5 |
| Cinnamic Alcohol (E) | 104-54-1 |
| Cinnamic Aldehyde (E) | 104-55-2 |
| Citronellol | 106-22-9 |
| Coumarin | 91-64-5 |
| Hydroxyisohexyl 3-cyclohexene carboxaldehyde (Cyclohexal/Lyral major) | 31906-04-4 |
| Hydroxyisohexyl 3-cyclohexene carboxaldehyde (Cyclohexal/Lyral minor) | 51414-25-6 |
| Damascenone Beta | 23696-85-7 |
| Damascone Alpha (E) | 24720-09-0 |
| Damascone Alpha (Z) | 23726-94-5 |
| Damascone Beta (E) | 23726-91-2 |
| Damascone Beta (Z) | 23726-92-3 |
| Damascone Delta cis/trans | 71048-83-4 |
| Damascone Delta trans/cis | n/a |
| Damascone Delta trans/trans | 71048-82-3 |
| Di Iso-Butyl Phthalate | 84-69-5 |
| Di isopentyl phthalate | 605-50-5 |
| Di Isopropyl Phthalate | 605-45-8 |
| Di n-Butyl Phthalate | 84-74-2 |
| Di n-pentyl phthalate | 131-18-0 |
| Dicyclohexyl phthalate | 84-61-7 |
| Diethyl Hexyl Phthalate | 117-81-7 |
| Diethyl Phthalate | 84-66-2 |
| Dimethyl Phthalate | 131-11-3 |
| Dimethyl Benzyl Carbinyl Acetate | 151-05-3 |
| Ebanol 1 | 67801-20-1 |
| Ebanol 2 | 67801-20-1 |
| Estragol | 140-67-0 |
| Eugenol | 97-53-0 |
| Eugenyl acetate | 93-28-7 |
| Farnesol (E)(E) | 106-28-5 |
| Farnesol (Z)(E) | 3790-71-4 |
| Farnesol (E)(Z) | 3879-60-5 |
| Farnesol (Z)(Z) | 16106-95-9 |
| Galaxolide (Cis) | 252933-49-6 |
| Galaxolide (Trans) | 252933-48-5 |
| Geranial | 141-27-5 |
| Geraniol | 106-24-1 |
| Geranyl Acetate | 105-87-3 |
| Hexadecanolide | 109-29-5 |
| Hexyl Cinnamic Aldehyde (E) | 101-86-0 |
| Hydroxycitronellal | 107-75-5 |
| Iso E Super Alpha | 68155-66-8 |
| Iso E Super Beta | 54464-57-2 |
| Iso E Super Gamma | 68155-67-9 |
| Iso E Super minor | 54464-59-4 |
| Isoeugenol (E) | 5932-68-3 |
| Isoeugenol (Z) | 5912-86-7 |
| Isoeugenyl Acetate | 93-29-8 |
| Lilial | 80-54-6 |
| Limonene | 5989-27-5 |
| Linalool | 78-70-6 |
| Linalyl Acetate | 115-95-7 |
| Majantol | 103694-68-4 |
| Menthol | 1490-04-6 |
| Methoxycoumarin-7 | 531-59-9 |
| Methyl Eugenol | 93-15-2 |
| Methyl Heptine Carbonate | 111-12-6 |
| Methyl Octine Carbonate | 111-80-8 |
| Methyl Salicylate | 119-36-8 |
| Neral | 106-26-3 |
| n-pentyl isopentyl phthalate | 84777-06-0 |
| Phenyl Acetaldehyde | 122-78-1 |
| Pinene Alpha | 80-56-8 |
| Pinene Beta | 127-91-3 |
| Propylidene Phthalide 3-(E) | 56014-72-3 |
| Propylidene Phthalide 3-(Z) | 94704-89-9 |
| Salicylaldehyde | 90-02-8 |
| Santalol Alpha | 115-71-9 |
| Santalol Beta | 77-42-9 |
| Sclareol | 515-03-7 |
| Terpinene Alpha | 99-86-5 |
| Terpineol Alpha | 98-55-5 |
| Terpineol Beta cis | 7299-41-4 |
| Terpineol Beta trans | 7299-40-3 |
| Terpineol Delta | 7299-42-5 |
| Terpineol Gamma | 586-81-2 |
| Terpinolene | 586-62-9 |
| Vanillin | 121-33-5 |

In a method according to the present disclosure, a complex mixture of perfume ingredients containing one or more of the known or suspected allergens recited in Table 1 may be separated in a comprehensive two-dimensional gas chromatography set-up, equipped with a dual-stage cryogenic modulator. A first separation is obtained on the first column and portions of the eluted, partly separated substances from this first column are accumulated and concentrated by a thermal modulator, before being re-injected into the second, much shorter column, where a second, much faster separation is achieved. The differences in separation times allows multiple second separations to be completed over the duration of the first separation. The concentration-release step in the thermal modulator is determined by the duration of separation in the second column. The set-up is furthermore completed by one detector, the function of which is to measure a signal directly related to the concentration of defined analytical targets in the eluted streams coming out of the secondary column. The output of such a 2D-GC set-up is a two-dimensional plot combining the information in a visual way. The elution sequence from the first column is reported on an x-axis (first dimension) of the plot, whereas the several elution sequences from the second column are reported on y-axes (second dimension), as show in FIG. 1 (From T. Dutriez, "GC×GC: a disruptive technique" in Gas Chromatography and 2D-GC chromatography for petroleum industry. F. Bertoncini, M. Courtiade-Tholance, D. Thiebaut (Editors) Editions Technip. 2013, p. 46).

Operating comprehensive gas chromatography equipment requires that a number parameters of the instrumental set-up are controlled. As will be apparent to a person skilled in the art, such parameters include the operating temperature and temperature program, injector split ratio, modulation period and column length and inner diameter.

In an embodiment of the invention, the temperature of the first column (main oven) is from sub-zero ° C. temperature to about 450° C., more particularly from about 30° C. to about 350° C. This temperature may be constant, but is generally increased at a given rate, starting from a temperature T0 and ending at a temperature Tn. The rate of heating is typically from about 0.1° C./min to about 25° C./min, more particularly from about 1° C./min to 15° C./min. The temperature program may also include one or more isothermal plateau at one or different pre-set temperature(s) and different heating rates may be combined within a given analytical process.

The temperature of the second column (secondary oven) may be identical to that of the first column or different. In an embodiment of the invention, the temperature of the secondary oven is from about 5° C. to about 35° C., more particularly from about 10 to about 30° C. higher than that of the main oven.

The injector split ratio, i.e. the ratio of the injected sample which effectively transferred to the first column, may be from about 1:1 to 1:150, more particularly from 1:75 to 1:125.

The modulation period, i.e. the time between two thermally-induced injections in the second column of the eluate coming out of the first column, is from about 2 to about 10 seconds, more particularly between 4 and 8 seconds. During the modulation period, the eluate coming out from the first column is cool-trapped or absorbed on a microporous material. The modulator may operate this action several time during the time a peak is eluting from the first column. This is expressed by the term $M_r$ in Equation 2.

In an embodiment of the invention, the eluate of the first column is cool-trapped at a temperature from about −150° C. to about to −70° C., more particularly from −120° C. to −80° C.

The clustering analysis methodology described herein provides that once a combination of stationary phases are found that satisfy the $SE_{2D}$ threshold value described hereinabove, a 2D-GC set-up containing that stationary phase combination will be able to resolve any of the 95 known or suspected allergens in any complex mixture of perfume ingredients.

The applicant surprisingly found that the desired Separation Efficiency ($SE_{2D}$) disclosed hereinabove of at least 94% and more particularly at least 95% can be achieved with a selection of stationary phases wherein the first stationary phase has an intermediate polarity, and the second stationary phase that is relatively polar compared with the first stationary phase. Such a selection of stationary phases is a preferred means to improve the resolution of the up to 95 known or suspected allergens set forth in Table 1.

Accordingly, in a particular embodiment of the invention there is provided a method of resolving defined known or suspected allergens contained in a complex mixture of perfume ingredients, said method comprising the steps of analyzing the complex mixture using two-dimensional gas chromatography, wherein the first stationary phase has an intermediate polarity, and the second stationary phase is relatively polar compared with the first stationary phase.

In a more particular embodiment the first stationary phase of intermediate polarity is an arylene-modified diphenyl-dimethyl siloxane copolymer stationary phase, more particularly having about 35% diphenylsiloxane moieties and about 65% dimethylsiloxane and arylene dimethyl siloxane moieties (Formula 1); and the second stationary phase that is relatively polar compared with the first is a (polyethyleneglycol) wax stationary phase. This combination of stationary phases provided good 2D separation efficiency for complex mixtures containing defined analytical targets of Table 1.

It was not expected that the first arylene-modified stationary phase would be useful because it is generally considered that arylene-modified stationary phases are highly specific to halogenated analytes, such as polychlorinated biphenyls and arochlor pesticides, and organophosphorous compounds.

Formula 1

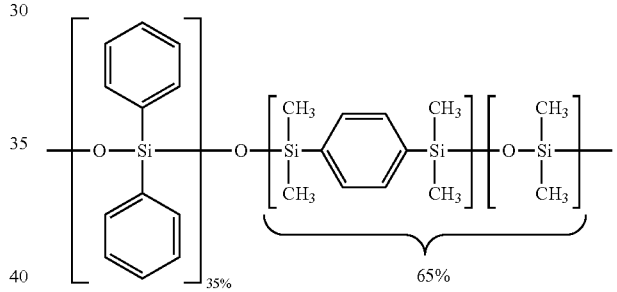

Alternative arylene-modified diphenyl- and arylene dimethyl siloxane copolymer stationary phases with different ratios of diphenylsiloxane and arylene dimethyl siloxane moieties (See Formula 2) such as Agilent DB-5 ms and Phenomenex ZEBRON ZB-5 ms (with X %=about 5% diphenylsiloxane and Y %=about 95% arylene dimethyl siloxane) are also useful as intermediate polarity first stationary phases Formula 2

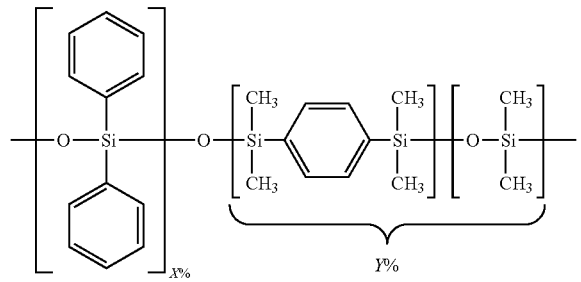

Other stationary phases can be employed as intermediate polarity first stationary phases, for example those having unmodified poly(diphenylsiloxane-co-dimethylsiloxane) with about 35% diphenylsiloxane moieties, but no arylene or phenylene groups in the backbone are similar to the herein above mentioned arylene-modified analogues. Examples of such intermediate polar stationary phases are commercially available under various brands and Trademarks, such as Agilent J&W VF-35 ms, Restek Rtx®-35, Restek Rtx®-35 ms, Restek Rxi®-35Sil MS, Supelco SPB-35, Alltech™ Heliflex™ AT™-35, Supelco Sup-Herb, VB-35-Valco-Bond®, SGC BPX-34, Phenomenex ZB-35 HT, and the like.

In further embodiments of the invention, the intermediate polarity first stationary phase is an arylene-modified stationary phase comprising from about 20 to about 60 wt % diphenylsiloxane moieties and about 40 to about 80 wt % arylene dimethyl siloxane moieties, more particularly from about 30 to about 40 wt % diphenylsiloxane groups and from about 60 to 70 wt % arylene dimethyl siloxane moieties, and still more particularly from about 33 to about 38 wt % diphenylsiloxane moieties and from about 62 to about 67 wt % arylene dimethyl siloxane moieties, wherein the weight percentage (wt %) is relative to the total weight of the polymer. Examples of such intermediate polarity stationary phases are Agilent J&W VF-35 ms, and Agilent DB-35 ms, and the like.

In a more particular embodiment, the intermediate polarity first stationary phase is Agilent J&W VF-35 ms.

In an embodiment of the invention, the polar stationary phase comprises a poly(ethylene oxide) polymer. Examples of such polar stationary phases are commercially available under various brands and Trademarks, such as Restek Rtx®-Wax, Restek Stabilwax, Agilent DB Wax, Agilent CB Wax SUPELCOWAX 10, SUPEROX II, SGE BP-20, 007-CW, Carbowax, Phenomenex® ZB-WAX, Phenomenex® ZB-WAX plus, and the like.

In a particular embodiment, the polar stationary phase is Restek Stabil-Wax®.

In an embodiment of the invention, the length of the column containing the first stationary phase is between 30 and 70 m, more particularly between 50 and 60 m.

In an embodiment of the invention and the diameter of the column containing the first stationary phase is between 0.15 and 0.32 mm, more particularly between 0.2 and 0.25 mm.

In an embodiment of the invention, the thickness of the first stationary phase is between 0.05 and 1 micrometers, more particularly between 0.25 and 0.50 micrometers.

In an embodiment of the invention, the length of the column containing the second stationary phase is between 0.5 and 3 m, more particularly between 0.8 and 2 m. In an embodiment of the invention the diameter of the column containing the second stationary phase is between 0.05 and 0.25 mm, more particularly between 0.1 and 0.2 mm.

In an embodiment of the invention, the thickness of the second stationary phase is between 0.05 and 1 micrometers, more particularly between 0.1 and 0.5 micrometers.

Once separated according to the present invention, the analytical targets are detected by using a flame ionization detector, a mass spectrometry detector or any detector having a suitable detection sensitivity and, for example, capable of transforming the molecular flow coming out of the second column into an electrical signal that is proportional to the concentration of the analytical target in the flow. Additionally, a mass spectrometry detector is use to further identify the chemical nature of the analyte by breaking the molecules into electrical charged fragments, the mass of which can be, for example, quantified as a function of the time of flight of each fragment between the locus of ionization and a detection device. Ionization occurs, for example, by exposure of the analyte to an electrical field providing a ionization energy of from 10 to 100 eV (electron-volt), more particularly from 50 to 80 eV. More details about gas chromatography/mass spectrometry coupling may be found in the book of S. Bouchonnet, "Introduction to GC-MS Coupling", CRC Press, 2013, which is hereby incorporated by reference.

The method according to the present invention can be applied in a number of situations where a large number of defined analytical targets must be separated in view of their identification and/or quantification. Such complex mixtures include, but are not limited to perfumes, fragrances, flavours, petroleum hydrocarbons, polycyclic aromatic compounds, polychlorobiphenyls, pesticides, herbicides, metabolites, and the like.

Analytical methods described herein are particularly useful in helping perfumers to prepare compositions that are free or substantially free of any known or suspected allergens set forth in Table 1 hereinabove.

For perfume compositions that are intended to be employed in consumer products that are rinse-off products, such as personal care or cosmetic rinse-off products, it is preferred that if any of the known or suspected allergens are present, then each allergen should be present in amounts of 100 ppm or lower in a product. For products that are leave-on, the level of individual allergens preferably should not exceed 10 ppm in a product. Perfume compositions intended for rinse-off applications are considered to be substantially free of any known or suspected allergens if levels of individual allergens do not exceed 100 ppm in a product. Perfume compositions intended for leave-on applications are considered to be substantially free of any known or suspected allergens if levels of individual allergens do not exceed 10 ppm in a product.

FIGURES

Figure 2:
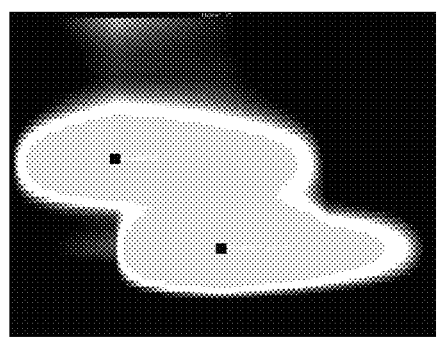

FIG. 1: Representation of neighbouring peaks on a 2D GC plot;

FIG. 2: Separation of Damascenone Beta and Damascone Alpha (VF35×Wax; $Rs_{2D}$=0.74). These two analytical targets are clustered, according to this invention.

Figure 3:
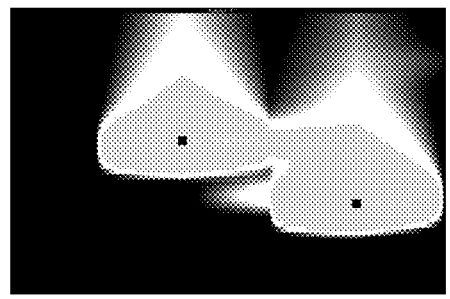

FIG. 3: Separation of Geranyl Acetate and Damascone Delta trans/trans (Rtx-5Sil×Wax; $Rs_{2D}$=0.93). These two analytical targets are clustered, according to this invention.

Figure 4:
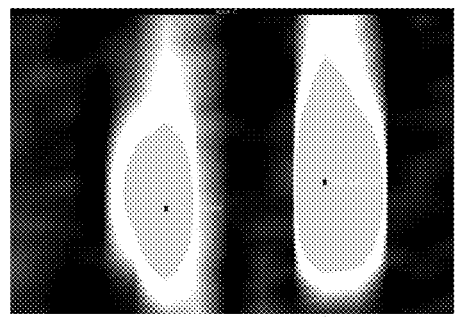

FIG. 4: Separation of Cyclohexal/Lyral minor and Cyclohexal/Lyral major (VF35×Wax; $Rs_{2D}$=1.23). These two analytical targets are Singletons, according to this invention.

Figure 5:
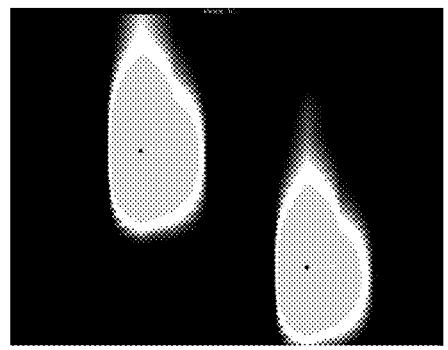

FIG. 5: Separation of Carvone and Geranial (VF35×Wax; $Rs_{2D}$=1.35). These two analytical targets are Singletons, according to this invention.

EXAMPLES

Example 1: Two-Dimensional Gas Chromatographic Procedure

The 95 ingredients reported in Table 1 (see description herein above) were dissolved in METHYL TERT-BUTYL ETHER at a level of 250 ppm (0.0250% by weight) each. In cases an ingredient was a mixture of isomers, the amount was adapted in such a way that the most abundant isomer was at a level of 250 ppm in the solution.

All GC×GC experiments were carried out using with a Pegasus 4D GC×GC-TOFMS from LECO (St. Joseph, Mich., USA), consisting of a 7890B GC from (Agilent Technologies, USA), a LN2 cooled thermal modulator from LECO and a Pegasus HT TOFMS from LECO. The MS part was operated in an EI mode at −70 eV, with an acquisition frequency set at 150 Hz in a mass ranging from 35 to 350 g/mol and with a multiple-plate voltage set at −1450 V. The GC transfer line was set at 245° C. and consisted of the secondary column. ChromaTOF (LECO) was used for controlling the 2D-GC set-up, for data acquisition and for data processing. Injections of the mixture of defined analytical targets were performed with a split injector with an injection temperature at 250° C., a split ratio at 1:100 and an injection volume of 0.5 μL. Carrier gas (Helium) was delivered at a constant flow (1.3 mL/min). For comparison purpose, the same first column geometry was used for all 2D-GC set-ups investigated (60 m×0.25 mm ID, 0.25 μm film thickness). The reference length of the secondary column was set at 1 m (150 mm ID, 0.15 μm film thickness) and was possibly extended to 2 m in case of available 2D space with reference comparison parameters. Connections between the primary and the two secondary columns were done by a SilTite® μ-Union (SGE Ringwood, Victoria, Australia). The reference 2D modulation period was set at 5 s with a hot pulse at 1.2 s (+15° C. versus the secondary column) and 2D modulation period was possibly extended to 7 s in case of wrap-around in secondary dimension with the reference comparison parameters.

A GC program-temperature ramp was implemented from 50° C. (1 min) to 245° C. when the 2D-GC set-up contains a Wax column and 300° C. when not (for several minutes depending of each 2D-GC set-up) at 2° C./min (see Table 2). A reference temperature offset for the secondary column was set at +15° C. versus the main oven and was possibly extended to +25° C. m in case of wrap-around in secondary dimension with reference comparison parameters. Secondary dimension retention times were corrected with an offset from −0.5 s to −1.0 s in order to maximize the available 2D space. The exact set of parameters for each combination of stationary phases are reported in Table 2.

Examples 2 to 6: Separation of Defined Analytical Targets

The result of the two-dimensional gas chromatographic separation of the 95 allergens are reported in Tables 3 to 7 are the experimental data, including retention times in both first ($^1$tr) and second ($^2$tr) dimensions, width of the peak at half height in the second dimension ($^2$width), and the resolution between neighboring peaks ($Rs_{2D}$, from the first closest neighbouring peak to the fifth closest neighbouring peak).

Legend of Tables 3 to 7:
$^1$tr=First Dimension Time (s)
$^2$tr=Second Dimension Time (s)
$^2$Width=Full Width at Half Height on secondary dimension
$Rs_{2D}$ 1=$Rs_{2D}$ with the first neighbour
$Rs_{2D}$ 2=$Rs_{2D}$ with the second neighbour
$Rs_{2D}$ 3=$Rs_{2D}$ with the third neighbour
$Rs_{2D}$ 4=$Rs_{2D}$ with the fourth neighbor
$Rs_{2D}$ 5=$Rs_{2D}$ with the fifth neighbour
TC $SE_{2D}$=Total contribution to SE2D. This total contribution is the sum of the $Rs_{2D}$ for the corresponding target.

Table 8 shows an example of how the ingredients are clustered, based on their $Rs_{2D}$ and $SE_{2D}$ values. The stationary phase combination was the same as in Table 3. The targets having neighbours with $Rs_{2D}$ larger than 1 are singleton and therefore not reported in Table 7. As apparent from the table, TERPINEOL BETA TRANS and TERPINEOL DELTA have, for example, a mutual of 0.78, which is smaller than 1, and therefore belong to the same cluster C1. TERPINEOL DELTA has an additional neighbour peak width a of 1.58, which is larger than 1 and therefore means that this peak is sufficiently apart from TERPINEOL DELTA not to be in a cluster with the latter. (Note that Table 2 shows that this third target is MENTHOL).

Table 9 shows a comprehensive list of clustered targets, meaning all peaks having at least one neighbouring peak with $Rs_{2D}$ smaller than 1.

Table 10 summarizes all results from Tables 3 to 7 with the values of and parameters in Equations 1, 2, 5, 6 and 7.

TABLE 2

Specific operating conditions for each 2D-GC set-up

| ID | 2D-GC set-ups | Modulation period (s) | Lenght of the secondary column (m) | Final temperature of the main oven (° C.) |
|---|---|---|---|---|
| 1 | Rtx-5Sil × Wax | 7 | 1 | 245 |
| 2 | Rtx-5Sil × Rtx-17Sil | 5 | 2 | 300 |
| 3 | Wax × Rtx-5Sil | 5 | 2 | 245 |
| 4 | VF35 × Wax | 5 | 1 | 245 |
| 5 | Rtx-17Sil × Wax | 5 | 1 | 245 |

| ID | 2D-GC set-ups | Duration time at final temperature (° C.) | Temperature offset of the secondary oven (° C.) | Second dimension time offset (s) |
|---|---|---|---|---|
| 1 | Rtx-5Sil × Wax | 20 | +25 | −0.5 |
| 2 | Rtx-5Sil × Rtx-17Sil | 10 | +15 | −1 |
| 3 | Wax × Rtx-5Sil | 35 | +15 | −1 |
| 4 | VF35 × Wax | 30 | +20 | −0.5 |
| 5 | Rtx-17Sil × Wax | 35 | +15 | −0.5 |

TABLE 3

Experimental data for Rtx5 × Wax stationary phase combination (Example 2)

| List of targets | $^1$tr | $^2$tr | $^2$Width | Rs$_{2D}$ 1 | Rs$_{2D}$ 2 | Rs$_{2D}$ 2 | Rs$_{2D}$ 4 | Rs$_{2D}$ 5 | TC SE$_{2D}$ |
|---|---|---|---|---|---|---|---|---|---|
| Acetyl Cedrene (main isomer) | 4235 | 0.633 | 0.036966 | 7.155109 | | | | | 1 |
| Alpha Isomethylionone | 3227 | 0.514 | 0.035604 | | | | | | 1 |
| Amyl Cinnamic Alcohol (E) | 3955 | 1.656 | 0.070874 | 4.178726 | 5.075817 | 5.137754 | | | 1 |
| Amyl Cinnamic Aldehyde (E) | 3829 | 0.923 | 0.047709 | 1.364748 | | | | | 1 |
| Amyl Salicylate (ISO-) | 3444 | 0.738 | 0.038064 | 1.047318 | | | | | 1 |
| Amyl Salicylate (N-) | 3584 | 0.777 | 0.039837 | 7.515063 | | | | | 1 |
| Anethole Trans (E) | 2499 | 0.963 | 0.053992 | 2.972017 | 12.76782 | | | | 1 |
| Anisyl Alcohol | 2478 | 4.837 | 0.18442 | 10.88749 | 12.76782 | | | | 1 |
| Benzaldehyde | 1148 | 1.359 | 0.070947 | | | | | | 1 |
| Benzyl Alcohol | 1435 | 4.467 | 0.17169 | 16.15586 | | | | | 1 |
| Benzyl Benzoate | 4228 | 1.623 | 0.071624 | 7.155109 | | | | | 1 |
| Benzyl Cinnamate (E) | 5187 | 2.104 | 0.083973 | 6.511547 | | | | | 1 |
| Benzyl Cyanide | 1869 | 2.943 | 0.12699 | | | | | | 1 |
| Benzyl Salicylate | 4543 | 1.728 | 0.071789 | | | | | | 1 |
| Camphor | 1925 | 0.586 | 0.044176 | 2.23663 | | | | | 1 |
| Carvone | 2331 | 0.85 | 0.04671 | 2.379768 | 4.297913 | | | | 1 |
| Caryophyllene Beta | 3038 | 0.303 | 0.031179 | | | | | | 1 |
| Cinnamic Alcohol (E) | 2576 | 4.302 | 0.16619 | | | | | | 1 |
| Cinnamic Aldehyde (E) | 2443 | 2.19 | 0.097562 | 8.205283 | | | | | 1 |
| Citronellol | 2247 | 0.949 | 0.047874 | | | | | | 1 |
| Coumarin | 3087 | 3.702 | 0.15304 | 12.86211 | | | | | 1 |
| Damascenone Beta | 2870 | 0.646 | 0.041526 | 0.900152 | 1.289077 | 1.494049 | 1.632791 | | 0.9001524 |
| Damascone Alpha (E) | 2912 | 0.567 | 0.039962 | 0.843133 | 1.200603 | 4.354721 | 16.06587 | | 0.84313277 |
| Damascone Alpha (Z) | 2772 | 0.494 | 0.032495 | 11.03334 | | | | | 1 |
| Damascone Beta (E) | 2982 | 0.58 | 0.037195 | 6.781579 | 11.11522 | | | | 1 |
| Damascone Beta (Z) | 2884 | 0.507 | 0.036201 | 1.036743 | 1.039212 | 1.200603 | 1.494049 | | 1 |
| Damascone Delta cis/trans | 2891 | 0.6 | 0.036428 | 0.843133 | 0.900152 | 1.036743 | | | 0.75894799 |
| Damascone Delta trans/cis | 2688 | 0.487 | 0.033275 | | | | | | 1 |
| Damascone Delta trans/trans | 2842 | 0.567 | 0.03833 | 0.93155 | 1.289077 | | | | 0.9315502 |
| Di Iso-Butyl Phthalate | 4501 | 0.969 | 0.048177 | | | | | | 1 |
| Di isopentyl phthalate | 5082 | 0.956 | 0.047532 | | | | | | 1 |
| Di Isopropyl Phthalate | 3836 | 1.095 | 0.052944 | 1.364748 | 3.041261 | 5.054776 | | | 1 |
| Di n-Butyl Phthalate | 4781 | 1.068 | 0.050811 | | | | | | 1 |
| Di n-pentyl phthalate | 5306 | 1.048 | 0.050069 | | | | | | 1 |
| Dicyclohexyl phthalate | 6195 | 3.279 | 0.13412 | | | | | | 1 |
| Diethyl Hexyl Phthalate | 6251 | 1.781 | 0.081122 | | | | | | 1 |
| Diethyl Phthalate | 3626 | 1.517 | 0.068273 | | | | | | 1 |
| Dimethyl Benzyl Carbinyl Acetate | 2618 | 0.692 | 0.050032 | | | | | | 1 |
| Dimethyl Phthalate | 3122 | 2.19 | 0.091771 | 1.526838 | 9.391394 | 9.738884 | | | 1 |
| Ebanol 1 | 3108 | 0.6 | 0.036457 | 1.108452 | 9.738884 | 10.95377 | 12.86211 | | 1 |
| Ebanol 2 | 3136 | 0.639 | 0.037954 | 1.108452 | 9.391394 | 10.62555 | | | 1 |
| Estragol | 2135 | 0.81 | 0.0464 | 0.515836 | 0.542744 | 0.788273 | 3.333814 | | 0.22069028 |
| Eugenol | 2758 | 2.223 | 0.090546 | 11.03334 | | | | | 1 |
| Eugenyl acetate | 3367 | 1.438 | 0.064632 | | | | | | 1 |
| Farnesol (E)(E) | 4053 | 0.89 | 0.045083 | 1.892172 | 12.56978 | | | | 1 |
| Farnesol (E)(Z) | 3983 | 0.86 | 0.053156 | 0 | 2.381348 | 5.075817 | | | 0 |
| Farnesol (Z)(E) | 3983 | 0.86 | 0.053156 | 0 | 2.295438 | 5.137754 | | | 0 |
| Farnesol (Z)(Z) | 3892 | 0.85 | 0.041714 | 3.008755 | 3.086871 | 3.306978 | 4.862365 | 5.076328 | 1 |
| Galaxolide (Cis) | 4459 | 0.613 | 0.039151 | 0.264398 | | | | | 0.26439839 |
| Galaxolide (Trans) | 4466 | 0.619 | 0.038465 | 0.264398 | | | | | 0.26439839 |
| Geranial | 2422 | 0.738 | 0.041848 | 8.205283 | | | | | 1 |
| Geraniol | 2345 | 1.154 | 0.05591 | 2.379768 | 6.469175 | | | | 1 |
| Geranyl Acetate | 2856 | 0.494 | 0.03541 | 0.93155 | 1.039212 | 1.632791 | | | 0.9315502 |
| Hexadecanolide | 4725 | 0.593 | 0.036262 | | | | | | 1 |
| Hexyl Cinnamic Aldehyde (E) | 4151 | 0.89 | 0.045452 | | | | | | 1 |
| Hydroxycitronellal | 2492 | 1.405 | 0.063091 | 2.972017 | 10.88749 | | | | 1 |
| Hydroxyisohexyl 3-cyclohexene carboxaldehyde (Cyclohexal/Lyral major) | 3892 | 1.53 | 0.067972 | 1.030023 | 4.862365 | 7.402963 | 7.452571 | 7.637425 | 1 |
| Hydroxyisohexyl 3-cyclohexene carboxaldehyde (Cyclohexal/Lyral minor) | 3864 | 1.524 | 0.064631 | 1.030023 | 3.041261 | 5.076328 | 7.6884 | 7.776542 | 1 |
| Iso E Super Alpha | 3997 | 0.606 | 0.035899 | 2.295438 | 2.381348 | | | | 1 |
| Iso E Super Beta | 3885 | 0.547 | 0.035541 | 0.772059 | 1.053415 | 3.086871 | 7.452571 | 7.6884 | 0.77205882 |
| Iso E Super Gamma | 3913 | 0.567 | 0.034613 | 1.053415 | 3.008755 | 4.277514 | 7.402963 | | 1 |
| Iso E Super minor | 3864 | 0.547 | 0.033905 | 0.772059 | 3.306978 | 5.054776 | 7.637425 | 7.776542 | 0.77205882 |
| Isoeugenol (E) | 3122 | 2.573 | 0.10497 | 1.526838 | 10.62555 | 10.95377 | | | 1 |
| Isoeugenol (Z) | 2961 | 2.349 | 0.087931 | 7.175595 | 11.11522 | | | | 1 |
| Isoeugenyl Acetate | 3689 | 1.642 | 0.072461 | | | | | | 1 |
| Lilial | 3416 | 0.758 | 0.043279 | 1.047318 | | | | | 1 |
| Limonene | 1421 | 0.256 | 0.032844 | 16.15586 | | | | | 1 |
| Linalool | 1715 | 0.718 | 0.042539 | | | | | | 1 |
| Linalyl Acetate | 2345 | 0.408 | 0.034534 | 4.297913 | 6.469175 | | | | 1 |
| Majantol | 2996 | 1.477 | 0.066846 | 6.781579 | | | | | 1 |
| Menthol | 2051 | 0.758 | 0.045037 | 1.581179 | | | | | 1 |

TABLE 3-continued

Experimental data for Rtx5 × Wax stationary phase combination (Example 2)

| List of targets | $^1$tr | $^2$tr | $^2$Width | Rs$_{2D}$ 1 | Rs$_{2D}$ 2 | Rs$_{2D}$ 2 | Rs$_{2D}$ 4 | Rs$_{2D}$ 5 | TC SE$_{2D}$ |
|---|---|---|---|---|---|---|---|---|---|
| Methoxycoumarin-7 | 4081 | 4.236 | 0.1644 | 11.3582 | 12.56978 | | | | 1 |
| Methyl Eugenol | 2940 | 1.068 | 0.052903 | 4.354721 | 7.175595 | 14.11996 | | | 1 |
| Methyl Heptine Carbonate | 2135 | 0.72 | 0.043148 | 0.788273 | 1.108792 | 1.261058 | 4.13508 | | 0.78827261 |
| Methyl Octine Carbonate | 2541 | 0.679 | 0.041633 | | | | | | 1 |
| Methyl Salicylate | 2114 | 1.233 | 0.055896 | 2.823862 | 3.333814 | 4.13508 | | | 1 |
| Neral | 2296 | 0.712 | 0.039618 | | | | | | 1 |
| n-pentyl isopentyl phthalate | 5194 | 1.002 | 0.048866 | 6.511547 | | | | | 1 |
| Phenyl Acetaldehyde | 1477 | 1.491 | 0.066865 | 1.510067 | | | | | 1 |
| Pinene Alpha | 1043 | 0.164 | 0.033474 | | | | | | 1 |
| Pinene Beta | 1218 | 0.21 | 0.038099 | | | | | | 1 |
| Propylidene Phthalide 3-(E) | 3570 | 1.979 | 0.085905 | 7.515063 | | | | | 1 |
| Propylidene Phthalide 3-(Z) | 3731 | 2.263 | 0.093138 | | | | | | 1 |
| Salicylaldehyde | 1484 | 1.761 | 0.075452 | 1.510067 | | | | | 1 |
| Santalol Alpha | 3934 | 1.022 | 0.050207 | 4.178726 | 4.277514 | | | | 1 |
| Santalol Beta | 4067 | 1.114 | 0.051404 | 1.892172 | 11.3582 | | | | 1 |
| Sclareol | 5516 | 1.689 | 0.072529 | | | | | | 1 |
| Terpinene Alpha | 1372 | 0.243 | 0.030979 | | | | | | 1 |
| Terpineol Alpha | 2128 | 0.864 | 0.048338 | 0.515836 | 0.823545 | 1.261058 | 2.823862 | | 0.42481459 |
| Terpineol Beta cis | 1932 | 0.831 | 0.042312 | 2.23663 | | | | | 1 |
| Terpineol Beta trans | 2009 | 0.956 | 0.046408 | 0.783489 | | | | | 0.78348909 |
| Terpineol Delta | 2023 | 0.89 | 0.041224 | 0.783489 | 1.581179 | | | | 0.78348909 |
| Terpineol Gamma | 2149 | 0.83 | 0.0447 | 0.542744 | 0.823545 | 1.108792 | | | 0.44697387 |
| Terpinolene | 1659 | 0.289 | 0.029896 | | | | | | 1 |
| Vanillin | 2926 | 6.619 | 0.25564 | 14.11996 | 16.06587 | | | | 1 |

TABLE 4

Experimental data for Rtx5 × Rx17 stationary phase combination (Example 3)

| List of targets | $^1$tr | $^2$tr | $^2$Width | Rs$_{2D}$ 1 | Rs$_{2D}$ 2 | Rs$_{2D}$ 2 | Rs$_{2D}$ 4 | Rs$_{2D}$ 5 | TC SE$_{2D}$ |
|---|---|---|---|---|---|---|---|---|---|
| Acetyl Cedrene (main isomer) | 4290 | 2.085 | 0.078985 | 4.21 | | | | | 1.00 |
| Alpha Isomethylionone | 3280 | 1.655 | 0.070744 | | | | | | 1.00 |
| Amyl Cinnamic Alcohol (E) | 4005 | 2.2 | 0.07523 | 2.11 | 3.33 | 3.40 | | | 1.00 |
| Amyl Cinnamic Aldehyde (E) | 3880 | 2.19 | 0.076798 | 1.09 | | | | | 1.00 |
| Amyl Salicylate (ISO-) | 3495 | 1.85 | 0.066083 | 1.68 | | | | | 1.00 |
| Amyl Salicylate (N-) | 3640 | 1.89 | 0.064649 | 5.29 | | | | | 1.00 |
| Anethole Trans (E) | 2555 | 2.07 | 0.067802 | 1.68 | 3.55 | | | | 1.00 |
| Anisyl Alcohol | 2535 | 2.735 | 0.084998 | 3.55 | 4.79 | | | | 1.00 |
| Benzaldehyde | 1190 | 1.96 | 0.083965 | | | | | | 1.00 |
| Benzyl Alcohol | 1480 | 2.11 | 0.079133 | 5.01 | | | | | 1.00 |
| Benzyl Benzoate | 4280 | 3.005 | 0.093454 | 4.21 | | | | | 1.00 |
| Benzyl Cinnamate (E) | 5245 | 3.33 | 0.1021 | 3.87 | | | | | 1.00 |
| Benzyl Cyanide | 1925 | 2.84 | 0.089987 | | | | | | 1.00 |
| Benzyl Salicylate | 4600 | 2.965 | 0.089558 | | | | | | 1.00 |
| Camphor | 1980 | 1.845 | 0.10754 | 1.66 | | | | | 1.00 |
| Carvone | 2380 | 2.035 | 0.075333 | 2.14 | 2.97 | 4.15 | | | 1.00 |
| Caryophyllene Beta | 3095 | 1.415 | 0.067419 | | | | | | 1.00 |
| Cinnamic Alcohol (E) | 2630 | 2.595 | 0.082422 | | | | | | 1.00 |
| Cinnamic Aldehyde (E) | 2495 | 2.74 | 0.083831 | 5.26 | | | | | 1.00 |
| Citronellol | 2300 | 1.375 | 0.061069 | | | | | | 1.00 |
| Coumarin | 3140 | 3.785 | 0.11183 | 10.56 | | | | | 1.00 |
| Damascenone Beta | 2925 | 1.885 | 0.07937 | 1.03 | 1.03 | 1.50 | 2.15 | | 1.00 |
| Damascone Alpha (E) | 2965 | 1.795 | 0.07685 | 0.99 | 1.23 | 2.88 | 6.48 | | 0.99 |
| Damascone Alpha (Z) | 2825 | 1.715 | 0.078681 | 2.59 | | | | | 1.00 |
| Damascone Beta (E) | 3040 | 1.835 | 0.078473 | 1.00 | 2.86 | | | | 1.00 |
| Damascone Beta (Z) | 2940 | 1.777 | 0.038692 | 0.37 | 1.03 | 1.23 | 2.48 | | 0.37 |
| Damascone Delta cis/trans | 2945 | 1.82 | 0.08277 | 0.37 | 0.99 | 1.03 | 6.31 | | 0.37 |
| Damascone Delta trans/cis | 2740 | 1.655 | 0.077153 | | | | | | 1.00 |
| Damascone Delta trans/trans | 2900 | 1.715 | 0.075344 | 1.20 | 1.50 | | | | 1.00 |
| Di Iso-Butyl Phthalate | 4555 | 2.36 | 0.082806 | | | | | | 1.00 |
| Di isopentyl phthalate | 5140 | 2.36 | 0.08633 | | | | | | 1.00 |
| Di Isopropyl Phthalate | 3890 | 2.39 | 0.084574 | 1.09 | 1.51 | 2.83 | | | 1.00 |
| Di n-Butyl Phthalate | 4835 | 2.51 | 0.085801 | | | | | | 1.00 |
| Di n-pentyl phthalate | 5355 | 2.485 | 0.082997 | | | | | | 1.00 |
| Dicyclohexyl phthalate | 6255 | 3.825 | 0.11476 | | | | | | 1.00 |
| Diethyl Hexyl Phthalate | 6300 | 2.37 | 0.081362 | | | | | | 1.00 |
| Diethyl Phthalate | 3675 | 2.745 | 0.090351 | | | | | | 1.00 |
| Dimethyl Benzyl Carbinyl Acetate | 2670 | 1.83 | 0.075734 | | | | | | 1.00 |
| Dimethyl Phthalate | 3175 | 3.02 | 0.095451 | 2.92 | 7.80 | 7.86 | | | 1.00 |
| Ebanol 1 | 3160 | 1.43 | 0.063834 | 5.37 | 7.86 | 10.56 | | | 1.00 |

TABLE 4-continued

Experimental data for Rtx5 × Rx17 stationary phase combination (Example 3)

| List of targets | $^1$tr | $^2$tr | $^2$Width | Rs$_{2D}$ 1 | Rs$_{2D}$ 2 | Rs$_{2D}$ 2 | Rs$_{2D}$ 4 | Rs$_{2D}$ 5 | TC SE$_{2D}$ |
|---|---|---|---|---|---|---|---|---|---|
| Ebanol 2 | 3195 | 1.435 | 0.065157 | 5.26 | 7.80 | | | | 1.00 |
| Estragol | 2190 | 1.865 | 0.06567 | 0.46 | 1.61 | 1.69 | 1.69 | | 0.46 |
| Eugenol | 2815 | 2.215 | 0.075385 | 2.59 | | | | | 1.00 |
| Eugenyl acetate | 3420 | 2.58 | 0.084525 | | | | | | 1.00 |
| Farnesol (E)(E) | 4110 | 1.7 | 0.062999 | 1.78 | | | | | 1.00 |
| Farnesol (E)(Z) | 4035 | 1.655 | 0.064011 | 0.00 | 1.73 | 3.40 | | | 0.00 |
| Farnesol (Z)(E) | 4035 | 1.66 | 0.066779 | 0.00 | 1.68 | 3.33 | | | 0.00 |
| Farnesol (Z)(Z) | 3970 | 1.691 | 0.054276 | 1.23 | 1.37 | 1.67 | 4.00 | | 1.00 |
| Galaxolide (Cis) | 4515 | 2.22 | 0.083539 | 0.26 | | | | | 0.26 |
| Galaxolide (Trans) | 4520 | 2.235 | 0.082772 | 0.26 | | | | | 0.26 |
| Geranial | 2470 | 1.755 | 0.067246 | 5.26 | | | | | 1.00 |
| Geraniol | 2400 | 1.54 | 0.063025 | 1.50 | 2.97 | | | | 1.00 |
| Geranyl Acetate | 2910 | 1.525 | 0.060094 | 1.20 | 2.15 | 2.48 | | | 1.00 |
| Hexadecanolide | 4785 | 2.145 | 0.078587 | | | | | | 1.00 |
| Hexyl Cinnamic Aldehyde (E) | 4210 | 2.155 | 0.075698 | | | | | | 1.00 |
| Hydroxycitronellal | 2545 | 1.785 | 0.071342 | 1.68 | 4.79 | | | | 1.00 |
| Hydroxyisohexyl 3-cyclohexene carboxaldehyde (Cyclohexal/Lyral major) | 3945 | 2.34 | 0.079505 | 1.23 | 2.32 | 2.62 | 2.79 | 4.00 | 1.00 |
| Hydroxyisohexyl 3-cyclohexene carboxaldehyde (Cyclohexal/Lyral minor) | 3920 | 2.315 | 0.080616 | 1.23 | 1.51 | 2.24 | 2.50 | | 1.00 |
| Iso E Super Alpha | 4050 | 1.93 | 0.07364 | 1.68 | 1.73 | | | | 1.00 |
| Iso E Super Beta | 3945 | 1.88 | 0.076174 | 1.23 | 1.47 | 1.67 | 2.32 | 2.50 | 1.00 |
| Iso E Super Gamma | 3970 | 1.89 | 0.07261 | 1.02 | 1.23 | 1.23 | 2.62 | | 1.00 |
| Iso E Super minor | 3915 | 1.89 | 0.069418 | 1.47 | 2.24 | 2.79 | 2.83 | | 1.00 |
| Isoeugenol (E) | 3180 | 2.38 | 0.077226 | 2.92 | 5.26 | 5.37 | | | 1.00 |
| Isoeugenol (Z) | 3015 | 2.333 | 0.072664 | 1.01 | 2.86 | | | | 1.00 |
| Isoeugenyl Acetate | 3740 | 2.69 | 0.08576 | | | | | | 1.00 |
| Lilial | 3470 | 2.055 | 0.074164 | 1.68 | | | | | 1.00 |
| Limonene | 1475 | 1.055 | 0.08622 | 5.01 | | | | | 1.00 |
| Linalool | 1765 | 1.225 | 0.073398 | | | | | | 1.00 |
| Linalyl Acetate | 2395 | 1.295 | 0.066895 | 1.50 | 4.15 | | | | 1.00 |
| Majantol | 3050 | 2.005 | 0.07398 | 1.00 | | | | | 1.00 |
| Menthol | 2105 | 1.4 | 0.069163 | 1.77 | | | | | 1.00 |
| Methoxycoumarin-7 | 4145 | 4.14 | 0.12153 | 8.68 | | | | | 1.00 |
| Methyl Eugenol | 2995 | 2.285 | 0.078575 | 1.01 | 2.88 | 4.32 | | | 1.00 |
| Methyl Heptine Carbonate | 2185 | 1.8 | 0.067148 | 0.46 | 1.25 | 1.44 | 1.79 | | 0.46 |
| Methyl Octine Carbonate | 2595 | 1.77 | 0.064649 | | | | | | 1.00 |
| Methyl Salicylate | 2170 | 2.09 | 0.072635 | 1.61 | 1.79 | 2.82 | 3.12 | | 1.00 |
| Neral | 2355 | 1.71 | 0.069514 | 2.14 | | | | | 1.00 |
| n-pentyl isopentyl phthalate | 5250 | 2.416 | 0.083471 | 3.87 | | | | | 1.00 |
| Phenyl Acetaldehyde | 1525 | 2.22 | 0.08114 | 0.71 | | | | | 0.71 |
| Pinene Alpha | 1090 | 0.795 | 0.092236 | | | | | | 1.00 |
| Pinene Beta | 1265 | 0.965 | 0.098099 | | | | | | 1.00 |
| Propylidene Phthalide 3-(E) | 3625 | 2.925 | 0.090344 | 5.29 | | | | | 1.00 |
| Propylidene Phthalide 3-(Z) | 3785 | 3.175 | 0.096111 | | | | | | 1.00 |
| Salicylaldehyde | 1535 | 2.115 | 0.079171 | 0.71 | | | | | 0.71 |
| Santalol Alpha | 3990 | 1.84 | 0.067159 | 1.02 | 1.37 | 2.11 | | | 1.00 |
| Santalol Beta | 4125 | 1.985 | 0.07445 | 1.78 | 8.68 | | | | 1.00 |
| Sclareol | 5570 | 2.545 | 0.083208 | | | | | | 1.00 |
| Terpinene Alpha | 1420 | 1.035 | 0.083167 | | | | | | 1.00 |
| Terpineol Alpha | 2180 | 1.585 | 0.070044 | 0.98 | 1.25 | 1.69 | 2.82 | | 0.98 |
| Terpineol Beta cis | 1985 | 1.46 | 0.075841 | 1.66 | | | | | 1.00 |
| Terpineol Beta trans | 2060 | 1.545 | 0.076965 | 0.76 | | | | | 0.76 |
| Terpineol Delta | 2075 | 1.585 | 0.077601 | 0.76 | 1.77 | | | | 0.76 |
| Terpineol Gamma | 2200 | 1.58 | 0.07256 | 0.98 | 1.44 | 1.69 | 3.12 | | 0.98 |
| Terpinolene | 1715 | 1.23 | 0.07357 | | | | | | 1.00 |
| Vanillin | 2975 | 3.225 | 0.096758 | 4.32 | 6.31 | 6.48 | | | 1.00 |

TABLE 5

Experimental data for Wax × Rx5 stationary phase combination (Example 4)

| List of targets | $^1$tr | $^2$tr | $^2$Width | Rs$_{2D}$ 1 | Rs$_{2D}$ 2 | Rs$_{2D}$ 2 | Rs$_{2D}$ 4 | Rs$_{2D}$ 5 | TC SE$_{2D}$ |
|---|---|---|---|---|---|---|---|---|---|
| Acetyl Cedrene (main isomer) | 4415 | 2.11 | 0.065 | | | | | | 1.00 |
| Alpha Isomethylionone | 3310 | 2.08 | 0.064 | 9.11 | | | | | 1.00 |
| Amyl Cinnamic Alcohol (E) | 5185 | 0.915 | 0.037 | 0.76 | 3.84 | | | | 0.76 |
| Amyl Cinnamic Aldehyde (E) | 4490 | 1.335 | 0.047 | 4.12 | 6.05 | | | | 1.00 |
| Amyl Salicylate (ISO-) | 3880 | 1.545 | 0.050 | 1.34 | 5.19 | 7.74 | | | 1.00 |

TABLE 5-continued

Experimental data for Wax × Rx5 stationary phase combination (Example 4)

| List of targets | $^1$tr | $^2$tr | $^2$Width | $Rs_{2D}$ 1 | $Rs_{2D}$ 2 | $Rs_{2D}$ 2 | $Rs_{2D}$ 4 | $Rs_{2D}$ 5 | TC $SE_{2D}$ |
|---|---|---|---|---|---|---|---|---|---|
| Amyl Salicylate (N-) | 4075 | 1.49 | 0.049 | | | | | | 1.00 |
| Anethole Trans (E) | 3250 | 1.12 | 0.040 | 4.34 | | | | | 1.00 |
| Anisyl Alcohol | 4550 | 0.54 | 0.030 | 0.55 | 8.23 | | | | 0.55 |
| Benzaldehyde | 2230 | 0.75 | 0.036 | | | | | | 1.00 |
| Benzyl Alcohol | 3400 | 0.49 | 0.028 | 11.16 | | | | | 1.00 |
| Benzyl Benzoate | 5405 | 1.01 | 0.040 | | | | | | 1.00 |
| Benzyl Cinnamate (E) | 6865 | 1.62 | 0.055 | | | | | | 1.00 |
| Benzyl Cyanide | 3565 | 0.595 | 0.031 | | | | | | 1.00 |
| Benzyl Salicylate | 5760 | 1.04 | 0.039 | | | | | | 1.00 |
| Camphor | 2190 | 1.66 | 0.054 | | | | | | 1.00 |
| Carvone | 2945 | 1.245 | 0.043 | 0.51 | 5.93 | | | | 0.51 |
| Caryophyllene Beta | 2480 | 4.115 | 0.113 | | | | | | 1.00 |
| Cinnamic Alcohol (E) | 4560 | 0.56 | 0.031 | 0.55 | 8.08 | | | | 0.55 |
| Cinnamic Aldehyde (E) | 3895 | 0.73 | 0.033 | 7.17 | 7.74 | 12.28 | | | 1.00 |
| Citronellol | 3040 | 1.005 | 0.038 | 3.94 | 6.39 | 6.76 | | | 1.00 |
| Coumarin | 4985 | 0.665 | 0.033 | 3.52 | | | | | 1.00 |
| Damascenone Beta | 3220 | 1.595 | 0.052 | 1.56 | 4.34 | | | | 1.00 |
| Damascone Alpha (E) | 3130 | 1.795 | 0.057 | 0.31 | | | | | 0.31 |
| Damascone Alpha (Z) | 2830 | 2.075 | 0.064 | 6.84 | 6.98 | | | | 1.00 |
| Damascone Beta (E) | 3210 | 1.8 | 0.057 | 1.56 | | | | | 1.00 |
| Damascone Beta (Z) | 2975 | 2.03 | 0.064 | 5.17 | 5.93 | | | | 1.00 |
| Damascone Delta cis/trans | 3135 | 1.77 | 0.050 | 0.31 | | | | | 0.31 |
| Damascone Delta trans/cis | 2735 | 2.1 | 0.065 | 6.55 | 7.20 | 7.85 | | | 1.00 |
| Damascone Delta trans/trans | 3050 | 1.825 | 0.057 | 1.54 | 3.09 | 6.76 | | | 1.00 |
| Di Iso-Butyl Phthalate | 5195 | 1.33 | 0.048 | 3.84 | 4.32 | | | | 1.00 |
| Di isopentyl phthalate | 5700 | 1.49 | 0.052 | 12.72 | | | | | 1.00 |
| Di Isopropyl Phthalate | 4685 | 1.125 | 0.042 | 1.72 | 1.89 | 7.24 | | | 1.00 |
| Di n-Butyl Phthalate | 5550 | 1.295 | 0.047 | | | | | | 1.00 |
| Di n-pentyl phthalate | 5980 | 1.675 | 0.055 | | | | | | 1.00 |
| Dicyclohexyl phthalate | 5710 | 4.415 | 0.128 | 12.72 | | | | | 1.00 |
| Diethyl Hexyl Phthalate | 6905 | 4.105 | 0.126 | | | | | | 1.00 |
| Diethyl Phthalate | 4775 | 0.92 | 0.037 | 4.78 | 10.79 | | | | 1.00 |
| Dimethyl Benzyl Carbinyl Acetate | 3065 | 1.42 | 0.049 | 3.09 | 3.94 | 4.52 | | | 1.00 |
| Dimethyl Phthalate | 4595 | 0.74 | 0.034 | | | | | | 1.00 |
| Ebanol 1 | 3415 | 1.67 | 0.055 | 11.16 | | | | | 1.00 |
| Ebanol 2 | 3520 | 1.56 | 0.052 | | | | | | 1.00 |
| Estragol | 2735 | 1.215 | 0.041 | 0.95 | 2.01 | 6.55 | | | 0.95 |
| Eugenol | 4250 | 0.715 | 0.032 | | | | | | 1.00 |
| Eugenyl acetate | 4490 | 0.9 | 0.036 | 2.11 | 4.12 | | | | 1.00 |
| Farnesol (E)(E) | 4735 | 1.28 | 0.046 | 1.00 | 1.42 | 5.87 | 7.80 | | 1.00 |
| Farnesol (E)(Z) | 4660 | 1.26 | 0.046 | 1.52 | 1.72 | 5.86 | 6.10 | | 1.00 |
| Farnesol (Z)(E) | 4630 | 1.305 | 0.046 | 1.52 | 5.64 | 5.69 | | | 1.00 |
| Farnesol (Z)(Z) | 4530 | 1.307 | 0.043 | 8.08 | 8.23 | | | | 1.00 |
| Galaxolide (Cis) | 4640 | 2.11 | 0.065 | 0.75 | 5.69 | 6.10 | | | 0.75 |
| Galaxolide (Trans) | 4655 | 2.085 | 0.065 | 0.75 | 5.64 | 5.86 | 7.24 | | 0.75 |
| Geranial | 2940 | 1.295 | 0.045 | 0.51 | | | | | 0.51 |
| Geraniol | 3305 | 0.91 | 0.036 | 9.11 | | | | | 1.00 |
| Geranyl Acetate | 3020 | 1.76 | 0.056 | 1.54 | 3.48 | 6.39 | | | 1.00 |
| Hexadecanolide | 4765 | 2.5 | 0.078 | 6.58 | 7.80 | 10.79 | | | 1.00 |
| Hexyl Cinnamic Aldehyde (E) | 4750 | 1.43 | 0.050 | 1.42 | 4.78 | 6.58 | 7.12 | | 1.00 |
| Hydroxycitronellal | 3600 | 0.84 | 0.036 | | | | | | 1.00 |
| Hydroxyisohexyl 3-cyclohexene carboxaldehyde (Cyclohexal/Lyral major) | 5040 | 0.975 | 0.039 | 1.47 | | | | | 1.00 |
| Hydroxyisohexyl 3-cyclohexene carboxaldehyde (Cyclohexal/Lyral minor) | 5010 | 0.97 | 0.039 | 1.47 | 3.52 | | | | 1.00 |
| Iso E Super Alpha | 4135 | 2.145 | 0.066 | 9.59 | | | | | 1.00 |
| Iso E Super Beta | 3940 | 2.29 | 0.074 | 1.47 | | | | | 1.00 |
| Iso E Super Gamma | 3995 | 2.25 | 0.069 | | | | | | 1.00 |
| Iso E Super minor | 3910 | 2.29 | 0.067 | 1.47 | 5.19 | 5.51 | 12.28 | | 1.00 |
| Isoeugenol (E) | 4730 | 0.695 | 0.032 | 5.80 | 5.87 | 7.12 | | | 1.00 |
| Isoeugenol (Z) | 4490 | 0.715 | 0.033 | 2.11 | 6.05 | | | | 1.00 |
| Isoeugenyl Acetate | 4915 | 0.875 | 0.035 | 0.49 | 3.34 | | | | 0.49 |
| Lilial | 3905 | 1.475 | 0.049 | 1.34 | 5.51 | 7.17 | | | 1.00 |
| Limonene | 1070 | 2.72 | 0.075 | | | | | | 1.00 |
| Linalool | 2305 | 1.12 | 0.040 | | | | | | 1.00 |
| Linalyl Acetate | 2340 | 2.02 | 0.062 | | | | | | 1.00 |
| Majantol | 4140 | 0.905 | 0.036 | 9.59 | | | | | 1.00 |
| Menthol | 2620 | 1.25 | 0.044 | 1.82 | 5.32 | | | | 1.00 |
| Methoxycoumarin-7 | 6145 | 0.805 | 0.038 | | | | | | 1.00 |
| Methyl Eugenol | 3815 | 1.01 | 0.038 | | | | | | 1.00 |
| Methyl Heptine Carbonate | 2665 | 1.21 | 0.042 | 4.85 | | | | | 1.00 |
| Methyl Octine Carbonate | 3000 | 1.33 | 0.046 | 3.48 | 5.17 | | | | 1.00 |

TABLE 5-continued

Experimental data for Wax × Rx5 stationary phase combination (Example 4)

| List of targets | $^1$tr | $^2$tr | $^2$Width | $Rs_{2D}$ 1 | $Rs_{2D}$ 2 | $Rs_{2D}$ 2 | $Rs_{2D}$ 4 | $Rs_{2D}$ 5 | TC $SE_{2D}$ |
|---|---|---|---|---|---|---|---|---|---|
| Methyl Salicylate | 3090 | 0.95 | 0.036 | 4.52 | | | | | 1.00 |
| Neral | 2770 | 1.34 | 0.046 | 2.46 | 6.29 | | | | 1.00 |
| n-pentyl isopentyl phthalate | 5830 | 1.545 | 0.054 | | | | | | 1.00 |
| Phenyl Acetaldehyde | 2650 | 0.755 | 0.032 | 4.85 | 5.32 | | | | 1.00 |
| Pinene Alpha | 605 | 2.595 | 0.075 | | | | | | 1.00 |
| Pinene Beta | 805 | 2.745 | 0.078 | | | | | | 1.00 |
| Propylidene Phthalide 3-(E) | 4925 | 0.88 | 0.036 | 0.49 | 3.21 | | | | 0.49 |
| Propylidene Phthalide 3-(Z) | 5195 | 0.86 | 0.037 | 0.76 | 4.32 | | | | 0.76 |
| Salicylaldehyde | 2770 | 0.72 | 0.032 | 3.94 | 6.29 | | | | 1.00 |
| Santalol Alpha | 4715 | 1.255 | 0.045 | 1.00 | 1.89 | 5.80 | | | 1.00 |
| Santalol Beta | 4925 | 1.205 | 0.043 | 3.21 | 3.34 | | | | 1.00 |
| Sclareol | 6695 | 2.195 | 0.070 | | | | | | 1.00 |
| Terpinene Alpha | 1010 | 2.7 | 0.074 | | | | | | 1.00 |
| Terpineol Alpha | 2820 | 1.14 | 0.042 | 0.50 | 6.98 | | | | 0.50 |
| Terpineol Beta cis | 2590 | 1.135 | 0.040 | 1.82 | | | | | 1.00 |
| Terpineol Beta trans | 2765 | 1.075 | 0.039 | 1.52 | 2.01 | 2.46 | 3.94 | 7.85 | 1.00 |
| Terpineol Delta | 2735 | 1.115 | 0.042 | 0.95 | 1.52 | 7.20 | | | 0.95 |
| Terpineol Gamma | 2830 | 1.15 | 0.042 | 0.50 | 6.84 | | | | 0.50 |
| Terpinolene | 1350 | 2.72 | 0.075 | | | | | | 1.00 |
| Vanillin | 5260 | 0.515 | 0.030 | | | | | | 1.00 |

TABLE 6

Experimental data for Rtx-17 × Wax stationary phase combination (Example 5)

| List of targets | $^1$tr | $^2$tr | $^2$Width | $Rs_{2D}$ 1 | $Rs_{2D}$ 2 | $Rs_{2D}$ 2 | $Rs_{2D}$ 4 | $Rs_{2D}$ 5 | TC $SE_{2D}$ |
|---|---|---|---|---|---|---|---|---|---|
| Acetyl Cedrene (main isomer) | 4375 | 0.84 | 0.0424 | 1.98 | | | | | 1.00 |
| Alpha Isomethylionone | 3245 | 0.77 | 0.0409 | | | | | | 1.00 |
| Amyl Cinnamic Alcohol (E) | 4215 | 1.89 | 0.0749 | 1.36 | 2.52 | 4.64 | | | 1.00 |
| Amyl Cinnamic Aldehyde (E) | 4085 | 1.09 | 0.0503 | 1.62 | 2.19 | 2.43 | 4.45 | | 1.00 |
| Amyl Salicylate (ISO-) | 3550 | 1.01 | 0.0452 | 13.64 | | | | | 1.00 |
| Amyl Salicylate (N-) | 3710 | 1.04 | 0.0459 | 4.97 | | | | | 1.00 |
| Anethole Trans (E) | 2770 | 1.105 | 0.0469 | 1.81 | | | | | 1.00 |
| Anisyl Alcohol | 2985 | 3.8 | 0.1346 | 12.12 | 14.13 | | | | 1.00 |
| Benzaldehyde | 1465 | 1.435 | 0.0580 | | | | | | 1.00 |
| Benzyl Alcohol | 1775 | 4.275 | 0.1502 | | | | | | 1.00 |
| Benzyl Benzoate | 4730 | 1.51 | 0.0614 | | | | | | 1.00 |
| Benzyl Cinnamate (E) | 5730 | 3.085 | 0.1144 | 1.23 | | | | | 1.00 |
| Benzyl Cyanide | 2430 | 2.26 | 0.0858 | 8.05 | | | | | 1.00 |
| Benzyl Salicylate | 5010 | 1.66 | 0.0650 | | | | | | 1.00 |
| Camphor | 2100 | 0.77 | 0.0426 | 4.08 | | | | | 1.00 |
| Carvone | 2580 | 1.01 | 0.0468 | 0.42 | | | | | 0.42 |
| Caryophyllene Beta | 2865 | 0.525 | 0.0325 | 2.14 | 2.71 | | | | 1.00 |
| Cinnamic Alcohol (E) | 3030 | 3.635 | 0.1304 | 11.32 | 11.70 | 12.54 | 13.11 | | 1.00 |
| Cinnamic Aldehyde (E) | 2940 | 1.865 | 0.0728 | 7.40 | | | | | 1.00 |
| Citronellol | 2210 | 1.52 | 0.0635 | 2.05 | | | | | 1.00 |
| Coumarin | 3815 | 2.455 | 0.0939 | 5.77 | | | | | 1.00 |
| Damascenone Beta | 3035 | 0.85 | 0.0438 | 0.70 | 1.88 | 1.96 | 12.54 | | 0.70 |
| Damascone Alpha (E) | 3030 | 0.78 | 0.0404 | 0.70 | 2.32 | 2.60 | 13.11 | | 0.70 |
| Damascone Alpha (Z) | 2845 | 0.695 | 0.0378 | 0.80 | 2.14 | | | | 0.80 |
| Damascone Beta (E) | 3115 | 0.78 | 0.0409 | | | | | | 1.00 |
| Damascone Beta (Z) | 2990 | 0.705 | 0.0372 | 2.84 | 14.13 | | | | 1.00 |
| Damascone Delta cis/trans | 2925 | 0.795 | 0.0411 | 1.61 | 7.40 | | | | 1.00 |
| Damascone Delta trans/cis | 2725 | 0.71 | 0.0388 | 1.51 | | | | | 1.00 |
| Damascone Delta trans/trans | 2830 | 0.725 | 0.0359 | 0.80 | | | | | 0.80 |
| Di Iso-Butyl Phthalate | 4815 | 1.09 | 0.0487 | | | | | | 1.00 |
| Di isopentyl phthalate | 5365 | 1.28 | 0.0573 | | | | | | 1.00 |
| Di Isopropyl Phthalate | 4200 | 1.155 | 0.0509 | 2.26 | 3.37 | 3.45 | 4.64 | | 1.00 |
| Di n-Butyl Phthalate | 5135 | 1.155 | 0.0513 | | | | | | 1.00 |
| Di n-pentyl phthalate | 5615 | 1.665 | 0.0686 | | | | | | 1.00 |
| Dicyclohexyl phthalate | 7095 | 3.9 | 0.1302 | | | | | | 1.00 |
| Diethyl Hexyl Phthalate | 6680 | 2.935 | 0.1212 | | | | | | 1.00 |
| Diethyl Phthalate | 4105 | 1.4 | 0.0590 | 0.84 | 2.43 | 4.58 | | | 0.84 |
| Dimethyl Benzyl Carbinyl Acetate | 2780 | 0.9 | 0.0455 | 1.81 | | | | | 1.00 |
| Dimethyl Phthalate | 3700 | 1.765 | 0.0691 | 4.97 | | | | | 1.00 |
| Ebanol 1 | 3005 | 1 | 0.0472 | 1.96 | 2.32 | 2.84 | 11.70 | 12.12 | 1.00 |
| Ebanol 2 | 3050 | 1.055 | 0.0490 | 1.88 | 2.60 | 7.64 | 11.32 | | 1.00 |
| Estragol | 2335 | 0.995 | 0.0440 | 1.16 | | | | | 1.00 |
| Eugenol | 3075 | 2.37 | 0.0878 | 7.64 | | | | | 1.00 |

TABLE 6-continued

Experimental data for Rtx-17 × Wax stationary phase combination (Example 5)

| List of targets | $^1$tr | $^2$tr | $^2$Width | Rs$_{2D}$ 1 | Rs$_{2D}$ 2 | Rs$_{2D}$ 2 | Rs$_{2D}$ 4 | Rs$_{2D}$ 5 | TC SE$_{2D}$ |
|---|---|---|---|---|---|---|---|---|---|
| Eugenyl acetate | 3825 | 1.35 | 0.0568 | 5.77 | | | | | 1.00 |
| Farnesol (E)(E) | 4095 | 1.3 | 0.0563 | 0.84 | 1.62 | 3.14 | 3.80 | | 0.84 |
| Farnesol (E)(Z) | 4020 | 1.31 | 0.0573 | 0.25 | 1.19 | | | | 0.25 |
| Farnesol (Z)(E) | 4015 | 1.31 | 0.0573 | 0.25 | 1.06 | 4.36 | | | 0.25 |
| Farnesol (Z)(Z) | 3925 | 1.12 | 0.0477 | 3.24 | | | | | 1.00 |
| Galaxolide (Cis) | 4670 | 0.78 | 0.0410 | 0.49 | | | | | 0.49 |
| Galaxolide (Trans) | 4680 | 0.78 | 0.0416 | 0.49 | | | | | 0.49 |
| Geranial | 2580 | 0.96 | 0.0469 | 0.42 | | | | | 0.42 |
| Geraniol | 2390 | 1.68 | 0.0675 | 1.78 | | | | | 1.00 |
| Geranyl Acetate | 2895 | 0.73 | 0.0380 | 1.61 | 2.71 | | | | 1.00 |
| Hexadecanolide | 4850 | 0.8 | 0.0418 | 10.54 | | | | | 1.00 |
| Hexyl Cinnamic Aldehyde (E) | 4380 | 1.07 | 0.0495 | 1.98 | | | | | 1.00 |
| Hydroxycitronellal | 2675 | 1.72 | 0.0688 | | | | | | 1.00 |
| Hydroxyisohexyl 3-cyclohexene carboxaldehyde (Cyclohexal/Lyral major) | 4205 | 1.66 | 0.0671 | 1.16 | 1.23 | 1.36 | 3.37 | | 1.00 |
| Hydroxyisohexyl 3-cyclohexene carboxaldehyde (Cyclohexal/Lyral minor) | 4180 | 1.65 | 0.0666 | 1.23 | 1.30 | 1.46 | 3.45 | | 1.00 |
| Iso E Super Alpha | 4080 | 0.835 | 0.0414 | 2.19 | 3.80 | 4.58 | 6.52 | | 1.00 |
| Iso E Super Beta | 3960 | 0.77 | 0.0414 | 1.23 | 1.25 | | | | 1.00 |
| Iso E Super Gamma | 3985 | 0.795 | 0.0411 | 1.25 | 4.36 | 5.20 | | | 1.00 |
| Iso E Super minor | 3935 | 0.765 | 0.0392 | 1.23 | 3.24 | | | | 1.00 |
| Isoeugenol (E) | 3485 | 2.575 | 0.0945 | | | | | | 1.00 |
| Isoeugenol (Z) | 3310 | 2.375 | 0.0803 | 11.56 | | | | | 1.00 |
| Isoeugenyl Acetate | 4160 | 1.51 | 0.0615 | 1.30 | | | | | 1.00 |
| Lilial | 3640 | 0.93 | 0.0452 | | | | | | 1.00 |
| Limonene | 1240 | 0.435 | 0.0368 | | | | | | 1.00 |
| Linalool | 1630 | 1.215 | 0.0534 | | | | | | 1.00 |
| Linalyl Acetate | 2265 | 0.675 | 0.0368 | | | | | | 1.00 |
| Majantol | 3205 | 1.785 | 0.0707 | | | | | | 1.00 |
| Menthol | 1995 | 1.22 | 0.0532 | | | | | | 1.00 |
| Methoxycoumarin-7 | 4865 | 2.71 | 0.1007 | 10.54 | | | | | 1.00 |
| Methyl Eugenol | 3315 | 1.1 | 0.0495 | 11.56 | | | | | 1.00 |
| Methyl Heptine Carbonate | 2345 | 0.88 | 0.0421 | 1.16 | | | | | 1.00 |
| Methyl Octine Carbonate | 2720 | 0.865 | 0.0429 | 1.51 | | | | | 1.00 |
| Methyl Salicylate | 2390 | 1.4 | 0.0556 | 1.78 | | | | | 1.00 |
| Neral | 2440 | 0.925 | 0.0444 | 8.05 | | | | | 1.00 |
| n-pentyl isopentyl phthalate | 5485 | 1.455 | 0.0625 | | | | | | 1.00 |
| Phenyl Acetaldehyde | 1865 | 1.475 | 0.0626 | | | | | | 1.00 |
| Pinene Alpha | 825 | 0.285 | 0.0310 | | | | | | 1.00 |
| Pinene Beta | 1040 | 0.35 | 0.0346 | | | | | | 1.00 |
| Propylidene Phthalide 3-(E) | 4070 | 1.77 | 0.0714 | 3.14 | 4.45 | 6.52 | | | 1.00 |
| Propylidene Phthalide 3-(Z) | 4290 | 1.895 | 0.0721 | | | | | | 1.00 |
| Salicylaldehyde | 1815 | 1.84 | 0.0692 | | | | | | 1.00 |
| Santalol Alpha | 4005 | 1.45 | 0.0595 | 1.06 | 1.19 | 5.20 | | | 1.00 |
| Santalol Beta | 4200 | 1.475 | 0.0603 | 1.16 | 1.46 | 2.26 | 2.52 | | 1.00 |
| Sclareol | 5745 | 2.8 | 0.1114 | 1.23 | | | | | 1.00 |
| Terpinene Alpha | 1205 | 0.415 | 0.0362 | | | | | | 1.00 |
| Terpineol Alpha | 2175 | 1.245 | 0.0536 | 0.98 | | | | | 0.98 |
| Terpineol Beta cis | 1940 | 1.24 | 0.0536 | | | | | | 1.00 |
| Terpineol Beta trans | 2060 | 1.33 | 0.0530 | 1.58 | | | | | 1.00 |
| Terpineol Delta | 2090 | 1.255 | 0.0513 | 1.58 | 4.08 | | | | 1.00 |
| Terpineol Gamma | 2195 | 1.235 | 0.0534 | 0.98 | 2.05 | | | | 0.98 |
| Terpinolene | 1545 | 0.48 | 0.0348 | | | | | | 1.00 |
| Vanillin | 3540 | 4.595 | 0.1610 | 13.64 | | | | | 1.00 |

TABLE 7

Experimental data for VF35-MS × Wax stationary phase combination (Example 6)

| List of targets | $^1$tr | $^2$tr | $^2$Width | Rs$_{2D}$ 1 | Rs$_{2D}$ 2 | Rs$_{2D}$ 2 | Rs$_{2D}$ 4 | Rs$_{2D}$ 5 | TC SE$_{2D}$ |
|---|---|---|---|---|---|---|---|---|---|
| Acetyl Cedrene (main isomer) | 4470 | 0.695 | 0.038827 | 2.21 | | | | | 1.00 |
| Alpha Isomethylionone | 3375 | 0.61 | 0.036351 | 11.16 | | | | | 1.00 |
| Amyl Cinnamic Alcohol (E) | 4280 | 1.675 | 0.061175 | 0.79 | 1.50 | 3.21 | | | 0.79 |
| Amyl Cinnamic Aldehyde (E) | 4150 | 0.94 | 0.045905 | 1.35 | 1.38 | 2.38 | 3.08 | 3.51 | 1.00 |
| Amyl Salicylate (ISO-) | 3665 | 0.825 | 0.040867 | 6.14 | | | | | 1.00 |
| Amyl Salicylate (N-) | 3825 | 0.85 | 0.042853 | 3.27 | | | | | 1.00 |
| Anethole Trans (E) | 2820 | 0.965 | 0.045055 | 2.35 | 4.06 | | | | 1.00 |
| Anisyl Alcohol | 3000 | 3.624 | 0.13571 | 14.02 | | | | | 1.00 |

TABLE 7-continued

Experimental data for VF35-MS × Wax stationary phase combination (Example 6)

| List of targets | $^1tr$ | $^2tr$ | $^2$Width | $Rs_{2D}$ 1 | $Rs_{2D}$ 2 | $Rs_{2D}$ 2 | $Rs_{2D}$ 4 | $Rs_{2D}$ 5 | TC $SE_{2D}$ |
|---|---|---|---|---|---|---|---|---|---|
| Benzaldehyde | 1510 | 1.285 | 0.057839 | | | | | | 1.00 |
| Benzyl Alcohol | 1820 | 3.984 | 0.142 | | | | | | 1.00 |
| Benzyl Benzoate | 4745 | 1.38 | 0.059077 | 5.94 | 6.00 | | | | 1.00 |
| Benzyl Cinnamate (E) | 5740 | 2.175 | 0.086254 | | | | | | 1.00 |
| Benzyl Cyanide | 2435 | 2.15 | 0.084839 | 5.37 | 8.23 | 8.96 | 10.91 | | 1.00 |
| Benzyl Salicylate | 5035 | 1.515 | 0.061639 | | | | | | 1.00 |
| Camphor | 2200 | 0.62 | 0.040015 | 3.77 | 4.24 | | | | 1.00 |
| Carvone | 2640 | 0.86 | 0.043668 | 1.35 | | | | | 1.00 |
| Caryophyllene Beta | 3050 | 0.38 | 0.029971 | 3.12 | 15.28 | | | | 1.00 |
| Cinnamic Alcohol (E) | 3040 | 3.49 | 0.12971 | 13.39 | 13.92 | 15.28 | | | 1.00 |
| Cinnamic Aldehyde (E) | 2945 | 1.755 | 0.072103 | 8.73 | | | | | 1.00 |
| Citronellol | 2350 | 1.225 | 0.05472 | | | | | | 1.00 |
| Coumarin | 3775 | 2.42 | 0.094431 | | | | | | 1.00 |
| Damascenone Beta | 3125 | 0.7 | 0.039164 | 0.74 | 0.76 | 1.99 | 9.29 | | 0.56 |
| Damascone Alpha (E) | 3130 | 0.63 | 0.037497 | 0.75 | 0.76 | 2.13 | 9.89 | | 0.57 |
| Damascone Alpha (Z) | 2955 | 0.56 | 0.03537 | 8.73 | | | | | 1.00 |
| Damascone Beta (E) | 3220 | 0.63 | 0.037841 | 2.24 | | | | | 1.00 |
| Damascone Beta (Z) | 3095 | 0.57 | 0.036877 | 1.26 | 1.99 | 10.39 | | | 1.00 |
| Damascone Delta cis/trans | 3115 | 0.645 | 0.038025 | 0.74 | 0.75 | 1.26 | 9.74 | | 0.56 |
| Damascone Delta trans/cis | 2845 | 0.565 | 0.036046 | 2.13 | 2.15 | 4.06 | | | 1.00 |
| Damascone Delta trans/trans | 3035 | 0.64 | 0.037202 | 1.15 | 3.12 | 13.39 | | | 1.00 |
| Di Iso-Butyl Phthalate | 4880 | 0.94 | 0.045613 | | | | | | 1.00 |
| Di isopentyl phthalate | 5435 | 0.97 | 0.046779 | | | | | | 1.00 |
| Di Isopropyl Phthalate | 4245 | 1.02 | 0.048296 | 1.53 | 3.16 | 3.34 | | | 1.00 |
| Di n-Butyl Phthalate | 5190 | 1.015 | 0.04802 | | | | | | 1.00 |
| Di n-pentyl phthalate | 5675 | 1.2 | 0.05484 | | | | | | 1.00 |
| Dicyclohexyl phthalate | 7010 | 3.125 | 0.14422 | | | | | | 1.00 |
| Diethyl Hexyl Phthalate | 6585 | 1.64 | 0.060233 | | | | | | 1.00 |
| Diethyl Phthalate | 4120 | 1.285 | 0.054237 | 0.71 | 1.68 | 1.70 | 3.08 | 5.56 | 0.71 |
| Dimethyl Benzyl Carbinyl Acetate | 2865 | 0.755 | 0.042792 | 2.13 | | | | | 1.00 |
| Dimethyl Phthalate | 3685 | 1.675 | 0.069177 | 6.14 | | | | | 1.00 |
| Ebanol 1 | 3160 | 0.785 | 0.041446 | 2.13 | | | | | 1.00 |
| Ebanol 2 | 3200 | 0.835 | 0.041854 | 2.24 | | | | | 1.00 |
| Estragol | 2410 | 0.84 | 0.04148 | 1.60 | 3.36 | 8.23 | | | 1.00 |
| Eugenol | 3120 | 2.135 | 0.082054 | 9.29 | 9.74 | 9.89 | 10.39 | | 1.00 |
| Eugenyl acetate | 3830 | 1.255 | 0.054525 | 3.27 | | | | | 1.00 |
| Farnesol (E)(E) | 4215 | 1.075 | 0.0498 | 1.53 | 2.98 | 3.85 | | | 1.00 |
| Farnesol (E)(Z) | 4140 | 1.1 | 0.051734 | 0.29 | 1.03 | 1.38 | 1.68 | 2.45 | 0.29 |
| Farnesol (Z)(E) | 4135 | 1.08 | 0.050734 | 0.29 | 1.00 | 1.35 | 1.70 | 2.71 | 0.29 |
| Farnesol (Z)(Z) | 4030 | 1.04 | 0.047734 | 4.00 | | | | | 1.00 |
| Galaxolide (Cis) | 4750 | 0.65 | 0.037368 | 0.74 | 5.94 | | | | 0.74 |
| Galaxolide (Trans) | 4765 | 0.65 | 0.037646 | 0.74 | 6.00 | | | | 0.74 |
| Geranial | 2665 | 0.8 | 0.041155 | 1.35 | | | | | 1.00 |
| Geraniol | 2505 | 1.395 | 0.060047 | 5.01 | | | | | 1.00 |
| Geranyl Acetate | 3015 | 0.585 | 0.034552 | 1.15 | 13.92 | 14.02 | | | 1.00 |
| Hexadecanolide | 4955 | 0.65 | 0.037108 | | | | | | 1.00 |
| Hexyl Cinnamic Aldehyde (E) | 4455 | 0.915 | 0.04388 | 2.21 | | | | | 1.00 |
| Hydroxycitronellal | 2765 | 1.47 | 0.062564 | | | | | | 1.00 |
| Hydroxyisohexyl 3-cyclohexene carboxaldehyde (Cyclohexal/Lyral major) | 4265 | 1.47 | 0.062262 | 1.23 | 1.50 | 2.24 | 3.34 | | 1.00 |
| Hydroxyisohexyl 3-cyclohexene carboxaldehyde (Cyclohexal/Lyral minor) | 4240 | 1.455 | 0.059895 | 1.23 | 2.98 | 3.16 | | | 1.00 |
| Iso E Super Alpha | 4190 | 0.675 | 0.036123 | 3.85 | 6.08 | | | | 1.00 |
| Iso E Super Beta | 4075 | 0.62 | 0.037266 | 1.23 | 1.25 | 7.59 | | | 1.00 |
| Iso E Super Gamma | 4100 | 0.645 | 0.037522 | 1.25 | 4.96 | 5.56 | 7.45 | | 1.00 |
| Iso E Super minor | 4050 | 0.615 | 0.038151 | 1.23 | 4.00 | 7.70 | | | 1.00 |
| Isoeugenol (E) | 3520 | 2.355 | 0.089013 | 6.92 | | | | | 1.00 |
| Isoeugenol (Z) | 3350 | 2.155 | 0.072906 | 7.59 | 11.16 | | | | 1.00 |
| Isoeugenyl Acetate | 4165 | 1.4 | 0.059895 | 2.45 | 2.71 | 3.51 | 6.08 | | 1.00 |
| Lilial | 3720 | 0.785 | 0.042075 | | | | | | 1.00 |
| Limonene | 1400 | 0.3 | 0.038526 | | | | | | 1.00 |
| Linalool | 1775 | 0.965 | 0.047271 | | | | | | 1.00 |
| Linalyl Acetate | 2405 | 0.52 | 0.033467 | 2.75 | 3.36 | 10.91 | | | 1.00 |
| Majantol | 3290 | 1.535 | 0.065928 | | | | | | 1.00 |
| Menthol | 2140 | 0.965 | 0.046888 | | | | | | 1.00 |
| Methoxycoumarin-7 | 4805 | 2.72 | 0.10329 | | | | | | 1.00 |
| Methyl Eugenol | 3335 | 0.995 | 0.047454 | 7.59 | | | | | 1.00 |
| Methyl Heptine Carbonate | 2435 | 0.735 | 0.039 | 1.60 | 2.75 | 4.16 | 8.96 | | 1.00 |
| Methyl Octine Carbonate | 2815 | 0.715 | 0.038717 | 2.15 | 2.35 | | | | 1.00 |
| Methyl Salicylate | 2455 | 1.215 | 0.054091 | 4.16 | 5.37 | | | | 1.00 |
| Neral | 2530 | 0.77 | 0.04091 | 5.01 | | | | | 1.00 |
| n-pentyl isopentyl phthalate | 5555 | 1.065 | 0.050681 | | | | | | 1.00 |

TABLE 7-continued

Experimental data for VF35-MS × Wax stationary phase combination (Example 6)

| List of targets | $^1$tr | $^2$tr | $^2$Width | $Rs_{2D}$ 1 | $Rs_{2D}$ 2 | $Rs_{2D}$ 2 | $Rs_{2D}$ 4 | $Rs_{2D}$ 5 | TC $SE_{2D}$ |
|---|---|---|---|---|---|---|---|---|---|
| Phenyl Acetaldehyde | 1895 | 1.335 | 0.061039 | 2.41 | | | | | 1.00 |
| Pinene Alpha | 970 | 0.18 | 0.029529 | | | | | | 1.00 |
| Pinene Beta | 1195 | 0.23 | 0.0377 | | | | | | 1.00 |
| Propylidene Phthalide 3-(E) | 4080 | 1.635 | 0.067658 | 7.45 | 7.59 | 7.70 | | | 1.00 |
| Propylidene Phthalide 3-(Z) | 4290 | 1.775 | 0.065563 | 0.79 | 2.24 | 3.58 | | | 0.79 |
| Salicylaldehyde | 1865 | 1.65 | 0.068457 | 2.41 | | | | | 1.00 |
| Santalol Alpha | 4125 | 1.195 | 0.052257 | 0.71 | 1.00 | 1.03 | 2.38 | 4.96 | 0.71 |
| Santalol Beta | 4305 | 1.235 | 0.055219 | 3.21 | 3.58 | | | | 1.00 |
| Sclareol | 5815 | 1.975 | 0.080211 | | | | | | 1.00 |
| Terpinene Alpha | 1350 | 0.285 | 0.038326 | | | | | | 1.00 |
| Terpineol Alpha | 2290 | 1.03 | 0.048384 | 1.24 | | | | | 1.00 |
| Terpineol Beta cis | 2065 | 1.01 | 0.045621 | | | | | | 1.00 |
| Terpineol Beta trans | 2180 | 1.1 | 0.051334 | 1.09 | 4.24 | | | | 1.00 |
| Terpineol Delta | 2200 | 1.04 | 0.047463 | 1.09 | 3.77 | | | | 1.00 |
| Terpineol Gamma | 2315 | 1.01 | 0.047373 | 1.24 | | | | | 1.00 |
| Terpinolene | 1695 | 0.35 | 0.033478 | | | | | | 1.00 |
| Vanillin | 3520 | 4.545 | 0.15927 | 6.92 | | | | | 1.00 |

TABLE 8

Example of clustering for Rtx5 × Wax stationary phase combination

| # | Classification # | Defined analytical targets | $^1$tr (s) | $^2$tr (s) | $Rs_{2D}$ <1 | $Rs_{2D}$ with neighbouring peaks | | | $SE_{2D}$ |
|---|---|---|---|---|---|---|---|---|---|
| 1 | C1 | TERPINEOL BETA TRANS | 2009 | 0.956 | 1 | 0.78 | | | 0.78 |
| 2 | C1 | TERPINEOL DELTA | 2023 | 0.890 | 1 | 0.78 | 1.58 | | 0.78 |
| 3 | C2, C3 | TERPINEOL ALPHA | 2128 | 0.864 | 1 | 0.52 | 0.82 | 1.26 | 0.42 |
| 4 | C2, C4, C5 | ESTRAGOL | 2135 | 0.810 | 1 | 0.52 | 0.54 | 0.79 | 0.22 |
| 5 | C5 | METHYL HEPTINE CARBONATE | 2135 | 0.720 | 1 | 0.79 | 1.11 | 1.26 | 0.79 |
| 6 | C3, C4 | TERPINEOL GAMMA | 2149 | 0.830 | 1 | 0.54 | 0.82 | 1.11 | 0.45 |
| 7 | C6 | DAMASCONE DELTA TRANS/TRANS | 2842 | 0.567 | 1 | 0.93 | 1.29 | | 0.93 |
| 8 | C6 | GERANYL ACETATE | 2856 | 0.494 | 0 | 0.93 | 1.04 | 1.63 | 0.93 |
| 9 | C7 | DAMASCENONE | 2870 | 0.646 | 1 | 0.90 | 1.29 | 1.49 | 0.90 |
| 10 | C7, C8 | DAMASCONE DELTA CIS/TRANS | 2891 | 0.600 | 1 | 0.84 | 0.90 | 1.04 | 0.76 |
| 11 | C8 | DAMASCONE ALPHA E | 2912 | 0.567 | 1 | 0.84 | 1.20 | 4.35 | 0.84 |
| 12 | C9 | ISO E SUPER MINOR | 3864 | 0.547 | 1 | 0.77 | 3.31 | 5.05 | 0.77 |
| 13 | C9 | ISO E SUPER BETA | 3885 | 0.547 | 1 | 0.77 | 1.05 | 3.09 | 0.77 |
| 14 | C10 | FARNESOL EZ | 3983 | 0.860 | 1 | 0.00 | 2.38 | 5.08 | 0.00 |
| 15 | C10 | FARNESOL ZE | 3983 | 0.860 | 1 | 0.00 | 2.30 | 5.14 | 0.00 |
| 16 | C11 | GALAXOLIDE 1 | 4459 | 0.613 | 1 | 0.26 | | | 0.26 |
| 17 | C11 | GALAXOLIDE 2 | 4466 | 0.619 | 1 | 0.26 | | | 0.26 |
| 18 | | Sum defined analytical targets with $Rs_{2D}$ < 1 | | | 17 | | | | |

TABLE 9

List of clustered targets

| Clustered Defined analytical targets | Rtx-5Sil × Wax | Rtx-5Sil × Rtx-17Sil | Wax × Rtx-5Sil | Rtx-17Sil × Wax | VF35 × Wax |
|---|---|---|---|---|---|
| Amyl Cinnamic Alcohol (E) | | | x | | x |
| Anisyl Alcohol | | | x | | |
| Carvone | | | x | x | |
| Cinnamic Alcohol (E) | | | x | | |
| Damascenone Beta | x | | | x | x |
| Damascone Alpha (E) | x | x | x | x | x |
| Damascone Alpha (Z) | | | | x | |
| Damascone Beta (Z) | | x | | | |
| Damascone Delta cis/trans | x | x | x | | x |

TABLE 9-continued

| Clustered Defined analytical targets | Rtx-5Sil × Wax | Rtx-5Sil × Rtx-17Sil | Wax × Rtx-5Sil | Rtx-17Sil × Wax | VF35 × Wax |
|---|---|---|---|---|---|
| Damascone Delta trans/trans | x | | | x | |
| Diethyl Phthalate | | | | x | x |
| Estragol | x | x | x | | |
| Farnesol (E)(E) | | | | x | |
| Farnesol (E)(Z) | x | x | | x | x |
| Farnesol (Z)(E) | x | x | | x | x |
| Galaxolide (Cis) | x | x | x | x | x |
| Galaxolide (Trans) | x | x | x | x | x |
| Geranial | | | x | x | |
| Geranyl Acetate | x | | | | |
| Iso E Super Beta | x | | | | |
| Iso E Super minor | x | | | | |
| Isoeugenyl Acetate | | | x | | |
| Methyl Heptine Carbonate | x | x | | | |
| Phenyl Acetaldehyde | | x | | | |
| Propylidene Phthalide 3-(E) | | | x | | |
| Propylidene Phthalide 3-(Z) | | | x | | x |
| Salicylaldehyde | | x | | | |
| Terpineol Alpha | x | x | x | x | |
| Terpineol Beta trans | x | x | | | |
| Terpineol Delta | x | x | x | | |
| Terpineol Gamma | x | x | | x | |

TABLE 10

Results and parameters of Equations 1, 2, 3, 4 and 5.

| | Rtx-5Sil × Wax | Rtx-5Sil × Rtx-17Sil | Wax × Rtx-5Sil | Rtx-17Sil × Wax | VF35 × Wax |
|---|---|---|---|---|---|
| Parameters in Equations 3 and 4 | | | | | |
| Number of defined analytical targets neighbor peaks with $Rs_{2D} < 1$, i.e. clustered defined analytical targets | 17 | 15 | 16 | 14 | 11 |
| Number of singletons, i.e. resolved defined analytical targets | 78 | 80 | 79 | 81 | 84 |
| Value of $SE_{2D}$ | 92.5 | 92.7 | 93.3 | 94.7 | 95.5 |
| Value of $''SE_{2D}$ | 7.5 | 7.3 | 6.7 | 5.3 | 4.5 |
| Parameters in Equation 5, 6 and 7 | | | | | |
| First eluting target on first dimension ($^1t_{first}$) | 1043 | 1090 | 605 | 825 | 970 |
| Last eluting target on first dimension ($^1t_{last}$) | 6251 | 6300 | 6905 | 7095 | 7010 |
| Modulation period (Pmod) | 7 | 5 | 5 | 5 | 5 |
| Observed first dimension peaks capacity ($^{1,obs}nc$) | 186 | 261 | 315 | 314 | 302 |
| First eluting target on second dimension ($^2t_{first}$) | 0.16 | 0.80 | 0.49 | 0.29 | 0.18 |
| Last eluting target on second dimension ($^2t_{last}$) | 6.62 | 4.14 | 4.42 | 4.60 | 4.55 |
| a in Equation 7 | 0.009545 | 0.004256 | 0.005142 | 0.00798 | 0.00844 |
| b in Equation 7 | 0.006944 | 0.018916 | 0.004442 | 0.006423 | 0.006174 |
| Observed second dimension peaks capacity ($^{2,obs}nc$) | 26.2 | 16.2 | 24.5 | 22.7 | 23.5 |
| Observed 2D dimension peaks capacity ($^{obs}nc_{2D}$) | 3097 | 2691 | 4913 | 4521 | 4527 |

Example 7: Clustering of Ingredients

Pictorial representations of separation patterns of close defined analytical targets obtained with 2D GC set-ups in accordance with Examples 2 through 6 were prepared and are shown in FIGS. 2 through 5.

The invention claimed is:

1. A method of resolving defined known or suspected allergens in a complex mixture of perfume ingredients the method comprising the step of:
   using two-dimensional gas chromatography, resolving defined known or suspected allergens in the complex mixture wherein, the combination of first and second stationary phases is selected on the basis of a clustering analysis of defined known or suspected allergens providing a Separation Efficiency parameter ($SE_{2D}$) of 94% or greater
   wherein $$SE_{2D} = \frac{100}{n+m} \times \left( n + \sum_{i=1}^{m} \left( \prod_{j=1}^{o} Rs_{2D,ij} \right) \right)$$

and wherein
   $Rs_{2D}$ is the two-dimensional resolution between two neighbouring peaks (a) and (b), corresponding to two different defined known or suspected allergens on a 2D-GC contour plot, given by the formula:

$$Rs_{2D} = \sqrt{\left( \frac{2 \times \Delta^1 tr}{2 \times (M_r + 1) \times P_M} \right)^2 + \left( \frac{2 \times \Delta^2 tr}{2.55 \times (^2FWHH_a + {}^2FWHH_b)} \right)^2}$$

and wherein
   $M_r$ is the average number of time each peak is sampled by the modulator, rounded to the upper value,
   $P_M$ is the 2D-GC modulation period in seconds, $\Delta^1 tr$ is the difference of retention times between two neighbouring peaks (a) and (b) on the first dimension (x-axis);
   $\Delta^2 tr$ is the difference of retention times between the same two neighbouring peaks (a) and (b) on the second dimension (y-axis); $^2FWHH_a$ is the second dimension peak width of a peak (a) at half height and $^2FWHH_b$ is the second dimension peak width of a peak (b) at half height;
   two defined known or suspected allergens having an $Rs_{2D}$ value of 1 or higher are well separated and are referred to as Singletons (S); and
   two defined known or suspected allergens having an $Rs_{2D}$ value of less than 1 are a cluster;
   and wherein
   n is the number of Singletons (S);
   m is the number of defined known or suspected allergens belonging to a cluster;
   o is the number of clusters for a given known or suspected allergens; and
   $Rs_{2D,ij}$ is the Rs2D value for a defined analytical target i in a given cluster j.

2. The method of claim 1 wherein the first stationary phase has an intermediate polarity, and the second stationary phase is relatively polar compared with the first stationary phase.

3. The method of claim 2 wherein the first stationary phase is an arylene-modified diphenyl-dimethyl siloxane copolymer stationary phase.

4. The method of claim 3 wherein arylene-modified diphenyl-dimethyl siloxane copolymer comprises 20 to about 60 wt % diphenylsiloxane moieties and about 40 to about 80 wt % arylene dimethyl siloxane moieties, wherein the weight percentage (wt %) is relative to the total weight of the copolymer.

5. The method of claim 4, wherein arylene-modified diphenyl-dimethyl siloxane copolymer comprises 30 to about 40 wt % diphenylsiloxane moieties and about 60 to about 70 wt % arylene dimethyl siloxane moieties, wherein the weight percentage (wt %) is relative to the total weight of the copolymer.

6. The method of claim 5, wherein arylene-modified diphenyl-dimethyl siloxane copolymer comprises 33 to about 38 wt % diphenylsiloxane moieties and about 62 to about 67 wt % arylene dimethyl siloxane moieties, wherein the weight percentage (wt %) is relative to the total weight of the copolymer.

7. The method of claim 3 wherein arylene-modified diphenyl-dimethyl siloxane copolymer is a copolymer comprising about 35% diphenylsiloxane moieties and about 65% dimethylsiloxane and arylene dimethyl siloxane moieties.

8. The method of claim 1, wherein the second stationary phase is a (polyethylene-glycol) wax.

9. The method of claim 1, wherein the known or suspected allergen is selected from the group consisting of: Acetyl Cedrene (main isomer) (32388-55-9); Alpha Isomethylionone (127-51-5); Amyl Cinnamic Alcohol (E) (101-85-9); Amyl Cinnamic Aldehyde (E) (122-40-7); Amyl Salicylate (ISO-) (87-20-7); Amyl Salicylate (N-) (2050-08-0); Anethole Trans (E) (4180-23-8); Anisyl Alcohol (105-13-5); Benzaldehyde (100-52-7); Benzyl Alcohol (100-51-6); Benzyl Benzoate (120-51-4); Benzyl Cinnamate (E) (103-41-3); Benzyl Cyanide (140-29-4); Benzyl Salicylate (118-58-1); Camphor (76-22-2); Carvone (99-49-0); Caryophyllene Beta (87-44-5); Cinnamic Alcohol (E) (104-54-1); Cinnamic Aldehyde (E) (104-55-2); Citronellol (106-22-9); Coumarin (91-64-5); Hydroxyisohexyl 3-cyclohexene carboxaldehyde (Cyclohexal/Lyral major) (31906-04-4); Hydroxyisohexyl 3-cyclohexene carboxaldehyde (Cyclohexal/Lyral minor) (51414-25-6); Damascenone Beta (23696-85-7); Damascone Alpha (E) (24720-09-0); Damascone Alpha (Z) (23726-94-5); Damascone Beta (E) (23726-91-2); Damascone Beta (Z) (23726-92-3); Damascone Delta cis/trans (71048-83-4); Damascone Delta trans/cis (n/a); Damascone Delta trans/trans (71048-82-3); Di Iso-Butyl Phthalate (84-69-5); Di isopentyl phthalate (605-50-5); Di Isopropyl Phthalate (605-45-8); Di n-Butyl Phthalate (84-74-2); Di n-pentyl phthalate (131-18-0); Dicyclohexyl phthalate (84-61-7); Diethyl Hexyl Phthalate (117-81-7); Diethyl Phthalate (84-66-2); Dimethyl Phthalate (131-11-3); Dimethyl Benzyl Carbinyl Acetate (151-05-3); Ebanol 1 (67801-20-1); Ebanol 2 (67801-20-1); Estragol (140-67-0); Eugenol (97-53-0); Eugenyl acetate (93-28-7); Farnesol (E)(E) (106-28-5); Farnesol (Z)(E) (3790-71-4); Farnesol (E)(Z) (3879-60-5); Farnesol (Z)(Z) (16106-95-9); Galaxolide (Cis) (252933-49-6); Galaxolide (Trans) (252933-48-5); Geranial (141-27-5); Geraniol (106-24-1); Geranyl Acetate (105-87-3); Hexadecanolide (109-29-5); Hexyl Cinnamic Aldehyde (E) (101-86-0); Hydroxycitronellal (107-75-5); Iso E Super Alpha (68155-66-8); Iso E Super Beta (54464-57-2); Iso E Super Gamma (68155-67-9); Iso E Super minor (54464-59-4); Isoeugenol (E) (5932-68-3); Isoeugenol (Z) (5912-86-7); Isoeugenyl Acetate (93-29-8); Lilial (80-54-6); Limonene (5989-27-5); Linalool (78-70-6); Linalyl Acetate (115-95-7); Majantol (103694-68-4); Menthol (1490-04-6); Methoxycoumarin-7 (531-59-9); Methyl Eugenol (93-15-2); Methyl Heptine Carbonate (111-12-6); Methyl Octine Carbonate (111-80-8); Methyl Salicylate (119-36-8); Neral (106-26-3); n-pentyl isopentyl phthalate (84777-06-0); Phenyl Acetaldehyde (122-78-1); Pinene Alpha (80-56-8); Pinene Beta (127-91-3); Propylidene Phthalide 3- (E) (56014-72-3); Propylidene Phthalide 3- (Z) (94704-89-9); Salicylaldehyde (90-02-8); Santalol Alpha (115-71-9); Santalol Beta (77-42-9); Sclareol (515-03-7); Terpinene Alpha (99-86-5); Terpineol Alpha (98-55-5); Terpineol Beta cis (7299-41-4); Terpineol Beta trans (7299-40-3); Terpineol Delta (7299-42-5); Terpineol Gamma (586-81-2); Terpinolene (586-62-9); and Vanillin (121-33-5).

10. The method of claim 1, wherein the complex mixture of perfume ingredients comprises at least one known or suspected allergen selected from the group consisting of: Acetyl Cedrene (main isomer) (32388-55-9); Alpha Isomethylionone (127-51-5); Amyl Cinnamic Alcohol (E) (101-85-9); Amyl Cinnamic Aldehyde (E) (122-40-7); Amyl Salicylate (ISO-) (87-20-7); Amyl Salicylate (N-) (2050-08-0); Anethole Trans (E) (4180-23-8); Anisyl Alcohol (105-13-5); Benzaldehyde (100-52-7); Benzyl Alcohol (100-51-6); Benzyl Benzoate (120-51-4); Benzyl Cinnamate (E) (103-41-3); Benzyl Cyanide (140-29-4); Benzyl Salicylate (118-58-1); Camphor (76-22-2); Carvone (99-49-0); Caryophyllene Beta (87-44-5); Cinnamic Alcohol (E) (104-54-1); Cinnamic Aldehyde (E) (104-55-2); Citronellol (106-22-9); Coumarin (91-64-5); Hydroxyisohexyl 3-cyclohexene carboxaldehyde (Cyclohexal/Lyral major) (31906-04-4); Hydroxyisohexyl 3-cyclohexene carboxaldehyde (Cyclohexal/Lyral minor) (51414-25-6); Damascenone Beta (23696-85-7); Damascone Alpha (E) (24720-09-0); Damascone Alpha (Z) (23726-94-5); Damascone Beta (E) (23726-91-2); Damascone Beta (Z) (23726-92-3); Damascone Delta cis/trans (71048-83-4); Damascone Delta trans/cis (n/a); Damascone Delta trans/trans (71048-82-3); Di Iso-Butyl Phthalate (84-69-5); Di isopentyl phthalate (605-50-5); Di Isopropyl Phthalate (605-45-8); Di n-Butyl Phthalate (84-74-2); Di n-pentyl phthalate (131-18-0); Dicyclohexyl phthalate (84-61-7); Diethyl Hexyl Phthalate (117-81-7); Diethyl Phthalate (84-66-2); Dimethyl Phthalate (131-11-3); Dimethyl Benzyl Carbinyl Acetate (151-05-3); Ebanol 1 (67801-20-1); Ebanol 2 (67801-20-1); Estragol (140-67-0); Eugenol (97-53-0); Eugenyl acetate (93-28-7); Farnesol (E)(E) (106-28-5); Farnesol (Z)(E) (3790-71-4); Farnesol (E)(Z) (3879-60-5); Farnesol (Z)(Z) (16106-95-9); Galaxolide (Cis) (252933-49-6); Galaxolide (Trans) (252933-48-5); Geranial (141-27-5); Geraniol (106-24-1); Geranyl Acetate (105-87-3); Hexadecanolide (109-29-5); Hexyl Cinnamic Aldehyde (E) (101-86-0); Hydroxycitronellal (107-75-5); Iso E Super Alpha (68155-66-8); Iso E Super Beta (54464-57-2); Iso E Super Gamma (68155-67-9); Iso E Super minor (54464-59-4); Isoeugenol (E) (5932-68-3); Isoeugenol (Z) (5912-86-7); Isoeugenyl Acetate (93-29-8); Lilial (80-54-6); Limonene (5989-27-5); Linalool (78-70-6); Linalyl Acetate (115-95-7); Majantol (103694-68-4); Menthol (1490-04-6); Methoxycoumarin-7 (531-59-9); Methyl Eugenol (93-15-2); Methyl Heptine Carbonate (111-12-6); Methyl Octine Carbonate (111-80-8); Methyl Salicylate (119-36-8); Neral (106-26-3); n-pentyl isopentyl phthalate (84777-06-0); Phenyl Acetaldehyde (122-78-1); Pinene Alpha (80-56-8); Pinene Beta (127-91-3); Propylidene Phthalide 3- (E) (56014-72-3); Propylidene Phthalide 3- (Z) (94704-89-9); Salicylaldehyde (90-02-8); Santalol Alpha (115-71-9); Santalol Beta (77-42-9); Sclareol (515-03-7); Terpinene Alpha (99-86-5); Terpineol Alpha (98-55-5); Terpineol Beta cis (7299-41-4); Terpineol Beta trans (7299-40-3); Terpineol Delta (7299-42-5); Terpineol Gamma (586-81-2); Terpinolene (586-62-9); and Vanillin (121-33-5).

11. A method of preparing a perfume composition, the method comprising the step of including in said composition at least one perfume ingredient that is either not a defined known or suspected allergen, or is an ingredient that is substantially free of defined known or suspected allergens, as determined by two-dimensional gas chromatography, wherein the combination of stationary phases for two-dimensional comprehensive gas chromatography are selected on the basis of the method of claim 1.

* * * * *